US012234575B1

(12) United States Patent
Agarwal et al.

(10) Patent No.: US 12,234,575 B1
(45) Date of Patent: Feb. 25, 2025

(54) DEVICES AND METHODS FOR NANOFIBER-BASED MEMBRANE FABRICATION

(71) Applicants: Arvind Agarwal, Miami, FL (US); Omar Blandon Cruz, Miami, FL (US); Lihua Lou, Miami, FL (US)

(72) Inventors: Arvind Agarwal, Miami, FL (US); Omar Blandon Cruz, Miami, FL (US); Lihua Lou, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/779,654

(22) Filed: Jul. 22, 2024

(51) Int. Cl.
| | | |
|---|---|---|
| *D01D 5/00* | (2006.01) | |
| *A61F 13/00* | (2006.01) | |
| *A61M 35/00* | (2006.01) | |
| *D01D 4/02* | (2006.01) | |

(52) U.S. Cl.
CPC ......... *D01D 4/02* (2013.01); *A61F 13/00063* (2013.01); *A61F 13/00987* (2013.01); *A61M 35/003* (2013.01); *A61M 35/10* (2019.05); *D01D 5/0038* (2013.01); *D01D 5/0084* (2013.01); *A61F 2013/0011* (2013.01); *A61F 2250/0067* (2013.01); *A61F 2250/0068* (2013.01); *D10B 2509/02* (2013.01); *D10B 2509/022* (2013.01)

(58) Field of Classification Search
CPC ......... A61F 13/0098; A61F 2250/0067; A61F 2250/0068; A61M 35/003; A61M 35/10; D01D 4/02; D01D 5/0038; D01D 5/0084; D10B 2509/02; D10B 2509/022

USPC .......... 264/465; 425/135, 145, 174.8 E, 464; 401/7; 604/290, 310
See application file for complete search history.

(56) References Cited

U.S. PATENT DOCUMENTS

| | | | | |
|---|---|---|---|---|
| 3,883,897 A | * | 5/1975 | Lefkowitz ........ | A41D 19/01594 401/7 |
| 4,953,998 A | * | 9/1990 | McCartherens ......... | A47K 7/03 401/7 X |

(Continued)

FOREIGN PATENT DOCUMENTS

| | | |
|---|---|---|
| CN | 203754859 U | 8/2014 |
| CN | 102776583 B | 11/2014 |
| CN | 104790049 B | 9/2016 |

(Continued)

OTHER PUBLICATIONS

Androitis, Eleftherios, G. et al. "Development of Water-Soluble Electrospun Fibers for the oral Delivery of Cannabinoids." AAPS PharmSciTech, 22, pp. 1-14, Jan. 5, 2021.

(Continued)

*Primary Examiner* — Leo B Tentoni
(74) *Attorney, Agent, or Firm* — SALIWANCHIK, LLOYD & EISENSCHENK

(57) ABSTRACT

Devices and methods for nanofiber-based membrane fabrication are provided. Portable (e.g., handheld) electrostatic spinning or electrospinning devices can be used for nanofiber-based membrane fabrication (e.g., wound care films or membranes, such as cannabidiol (CBD)-loaded films or membranes) and can be wearable and/or ultralow power. The device can include a needleless spinneret having solution supplied thereto and all powered by a low voltage battery.

20 Claims, 29 Drawing Sheets

(56) References Cited

U.S. PATENT DOCUMENTS

| | | |
|---|---|---|
| 6,753,454 B1 | 6/2004 | Smith et al. |
| 7,794,219 B2 | 9/2010 | Dubson et al. |

FOREIGN PATENT DOCUMENTS

| | | |
|---|---|---|
| CN | 110670150 A | 1/2020 |
| CN | 111575813 B | 10/2021 |
| CN | 215440775 U | 1/2022 |
| KR | 10-2022674 B1 | 9/2019 |
| WO | 2010/059127 A1 | 5/2010 |
| WO | 2016/024720 A1 | 2/2016 |
| WO | 2016/075688 A1 | 5/2016 |

OTHER PUBLICATIONS

Goroskaitė, Sandra et al. "The Formation and Analysis of Electrospun Materials from Nano-Microfibers with Hemp Extract." Doctoral Dissertation, Kaunas University of Technology, Faculty of Mechanical Engineering and Design, pp. 1-70, (Year: 2020).

\* cited by examiner

TOP VIEW
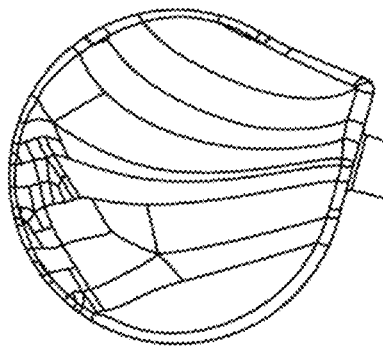
Solution flow control inlet (171)
LEFT VIEW
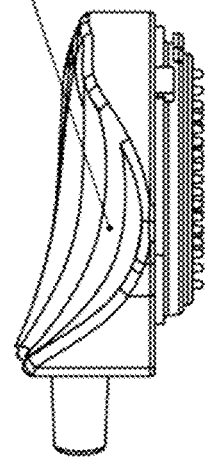
Needleless spinneret chamber (172)
170
FIG. 7

DEVICES AND METHODS FOR NANOFIBER-BASED MEMBRANE FABRICATION

BACKGROUND

Existing portable electrospinning devices have high input power and high flow rates while producing fibers with large diameters. The user is at risk of injury due to electric shock when holding the portable device. In addition, they typically use materials that are environmentally harmful.

BRIEF SUMMARY

Embodiments of the subject invention provide novel and advantageous devices and methods for nanofiber-based membrane fabrication. Portable (e.g., handheld) electrostatic spinning or electrospinning devices can be used for nanofiber-based membrane fabrication (e.g., wound care films or membranes, such as cannabidiol (CBD)-loaded films or membranes) and can be needleless, wearable, and/or ultralow power.

In an embodiment, an electrospinning device can comprise: a glove comprising an electrically insulating material and configured to be worn on a hand of a user; a needleless spinneret disposed on a first surface of the glove and configured to produce a nanofiber-based film from a solution by electrospinning; a solution delivery unit disposed on the glove and configured to contain the solution; a solution delivery conduit connecting the solution delivery unit to the needleless spinneret; and a voltage control portion configured to provide power to the electrospinning device. The electrospinning device can further comprise a solution flow control in operable communication with the solution delivery unit and configured to control a flow rate and/or a time of solution delivery from the solution delivery unit to the needleless spinneret during use. The solution flow control can be disposed on a second surface of the glove opposite from the first surface. The solution can be, for example, a polymer solution and can comprise at least one drug (e.g., CBD). The voltage control portion can comprise exactly one battery configured to provide a voltage of no more than 1.4 Volts (V) (e.g., nor more than 1 V) to the electrospinning device. The voltage control portion can be disposed on a rigid element disposed on a side surface of the glove. The voltage control portion can be the only power source on the electrospinning device (i.e., the electrospinning device can have no other (i.e., can explicitly omit) power sources other than the voltage control portion and a battery that may be connected thereto). The electrospinning device can further comprise a plurality of lights (e.g., light-emitting diodes (LEDs) disposed on the first surface of the glove. The solution delivery unit can be disposable (i.e., specifically designed for a single use). The electrospinning device can further comprise a spinneret fluid delivery coupler configured to couple the solution delivery conduit to the needleless spinneret. The needleless spinneret can comprise: a needless spinneret chamber configured to contain the solution; a plurality of conical spinneret nozzles on a bottom surface of the needleless spinneret; a plurality of fiber deposition boosters on the bottom surface of the needleless spinneret; and/or a solution flow control inlet coupled to the solution delivery conduit (either directly or via the spinneret fluid delivery coupler (if present)). The plurality of conical spinneret nozzles and the plurality of fiber deposition boosters can disposed as shown in FIG. 8 (e.g., including a configuration such that lines of conical spinneret nozzles alternate with fiber deposition boosters in a circumferential direction around the bottom surface of the needleless spinneret). The electrospinning device can further comprise a wrist support comprising a rigid material and disposed on at least the second surface of the glove. The electrospinning device can be configured to form a film from the solution at a flow rate in a range of, for example, from 0.07 nanoliters per hour (nl/h) to 0.8 nanoliters per minute (nl/min) (or any value or subrange therein).

In another embodiment, a method of forming a nanofiber-based film at a target site of a patient can comprise: providing an electrospinning device as disclosed herein (e.g., including any or all of the features from the previous paragraph); providing the solution to the solution delivery unit of the electrospinning device; wearing, by the user, the electrospinning device (e.g., on the user's hand); positioning the electrospinning device proximate to the target site such that a bottom surface of the needleless spinneret faces the target site; and operating the electrospinning device (e.g., using the needleless spinneret, the solution delivery unit, and/or the solution flow control) such that the needleless spinneret uses the solution and forms the film at the target site. The target site can be, for example, a wound site, a pain site, and/or a site of inflammation. The solution can be a polymer solution and can comprise at least one drug (e.g., CBD). The electrospinning device can operate using a total voltage of no more than 1.4 V (e.g., no more than 1 V). The needleless spinneret can form the film at the target site at a flow rate in a range of from, for example, 0.07 nl/h to 0.8 nl/min (or any value or subrange therein). The film can have a thickness in a range of, for example, from 1 nanometer (nm) to 100 micrometers (μm) (or any value or subrange therein, such as from 1 nm to 10 μm).

BRIEF DESCRIPTION OF DRAWINGS

FIG. 1 shows a perspective view in which the upper surface of the device can be seen.

FIG. 2 shows a perspective view in which the lower surface of the device can be seen.

FIG. 7 shows a top view (upper portion of FIG. 7) and left view (bottom portion of FIG. 7) of a needleless spinneret, according to an embodiment of the subject invention.

8) showing the bottom (right portion of FIG. 8) of a needleless spinneret, according to an embodiment of the subject invention.

Figure 9:
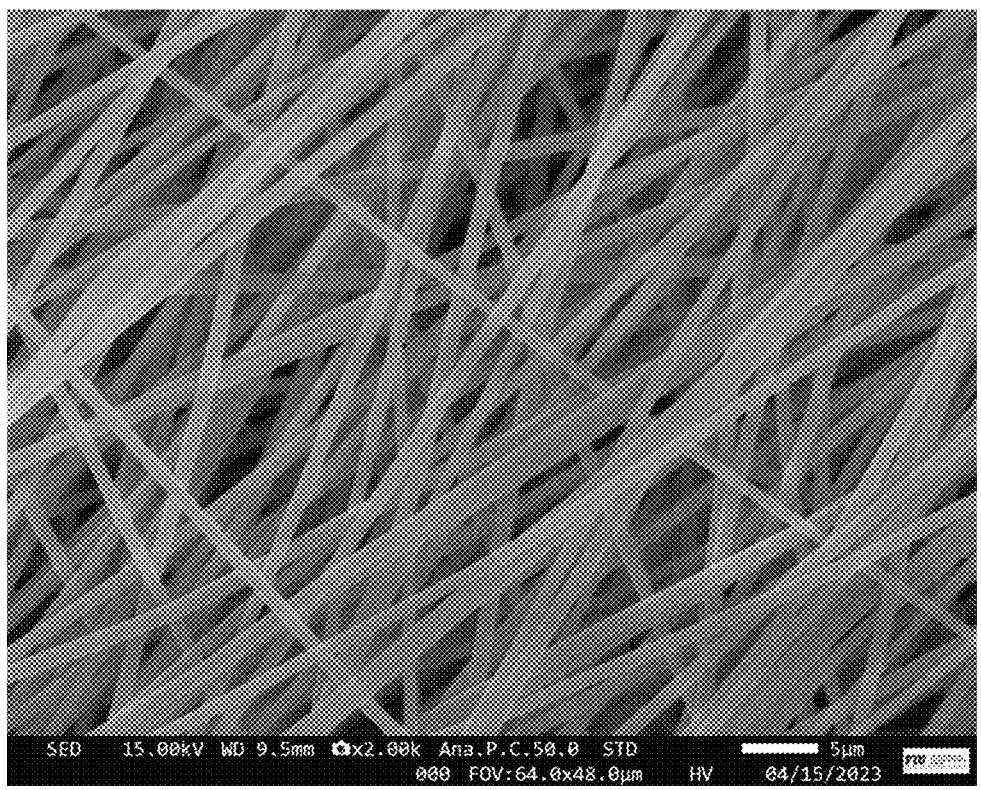

FIG. 9 shows a microscope image of a polyvinylpyrrolidone (PVP) fiber at a magnification of 2,000 times. The scale bar is 5 micrometers (μm).

Figure 10:
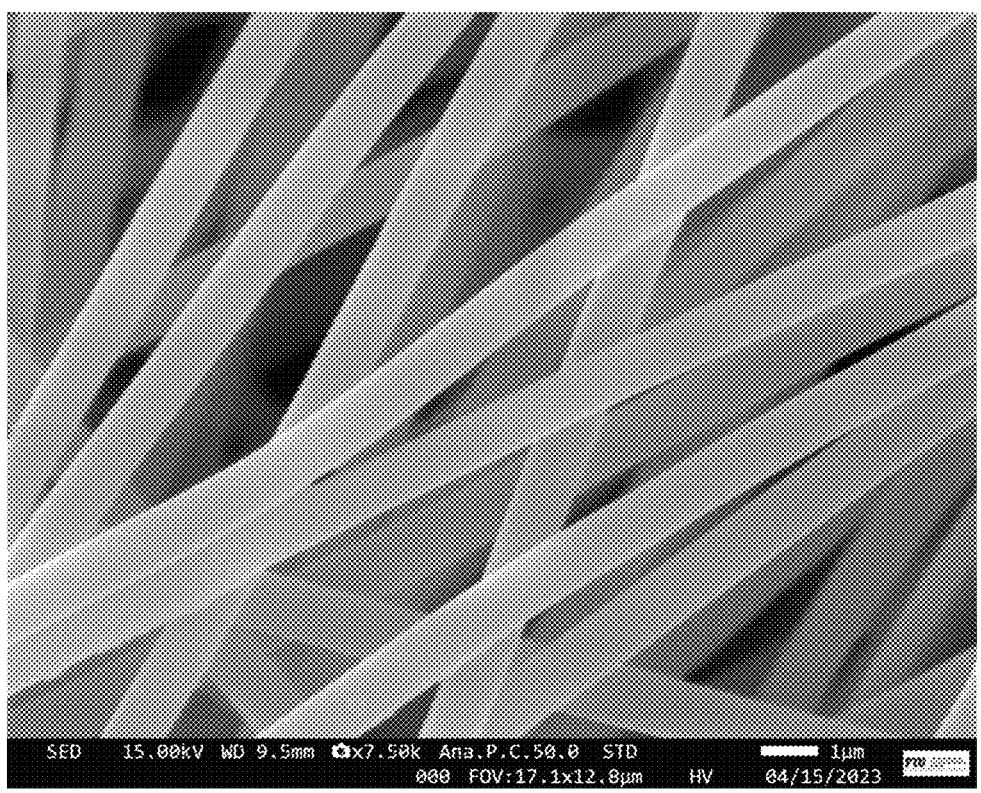

FIG. 10 shows a microscope image of a PVP fiber at a magnification of 7,500 times. The scale bar is 1 μm.

Figure 11:
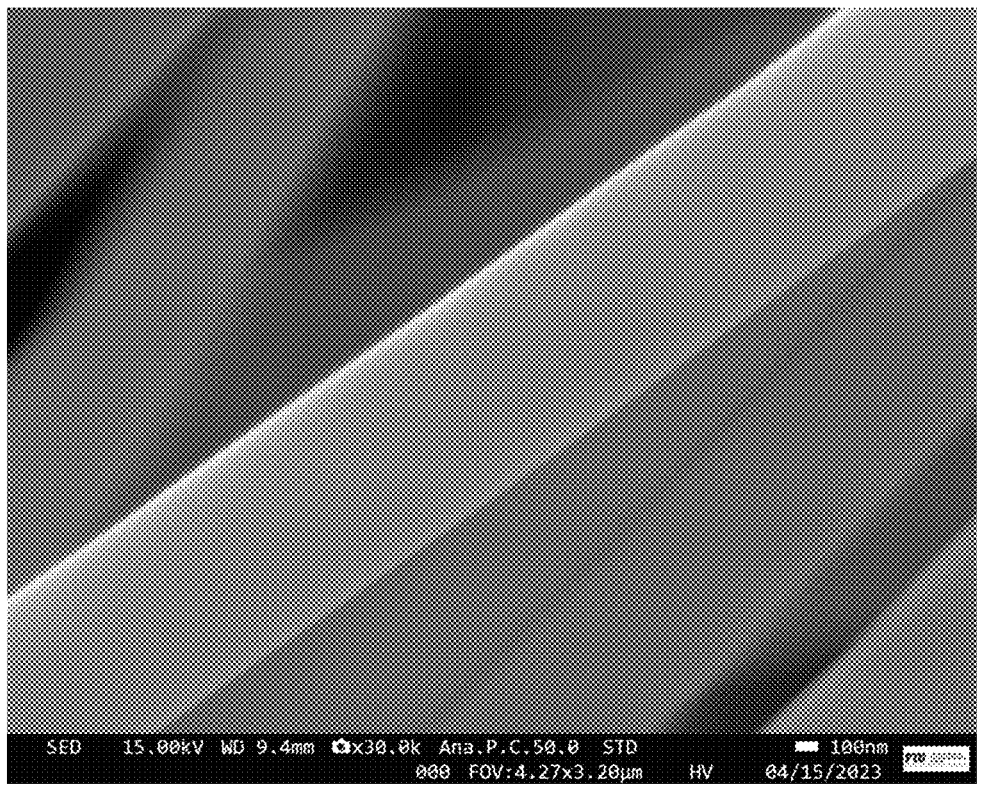

FIG. 11 shows a microscope image of a PVP fiber at a magnification of 30,000 times. The scale bar is 100 nanometers (nm).

Figure 12:
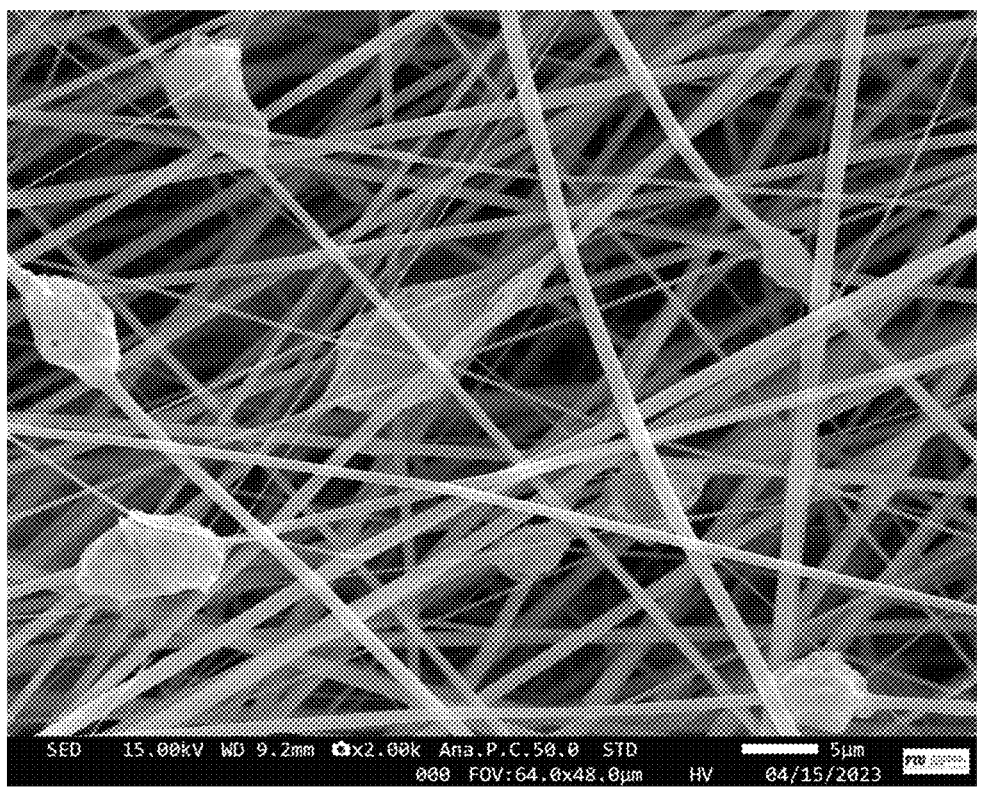

FIG. 12 shows a microscope image of a PVP/cannabidiol (CBD) (at a 1:1 ratio) (PVP/CBD 1:1) fiber at a magnification of 2,000 times. The scale bar is 5 μm.

Figure 13:
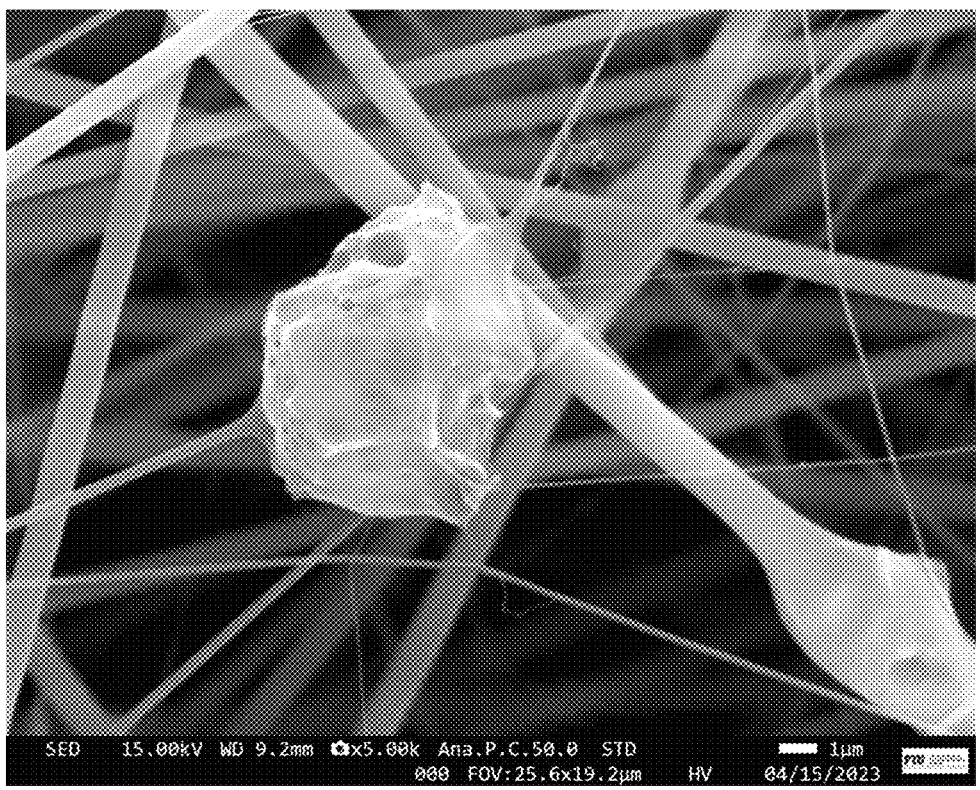

FIG. 13 shows a microscope image of a PVP/CBD 1:1 fiber at a magnification of 5,000 times. The scale bar is 1 μm.

Figure 14:
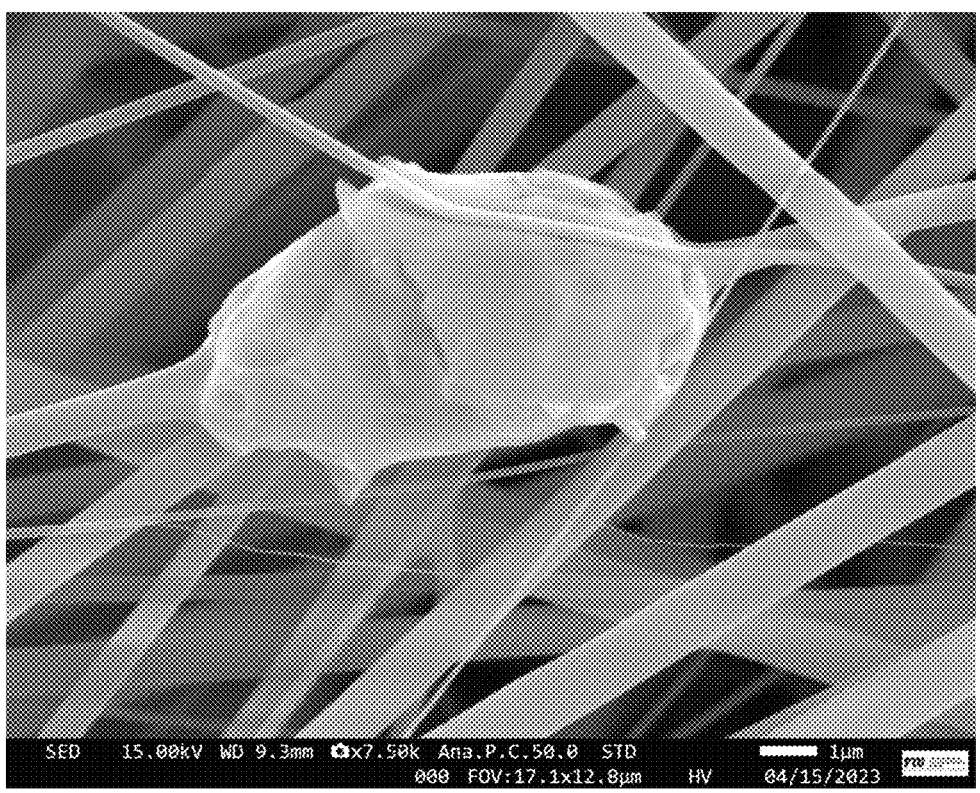

FIG. 14 shows a microscope image of a PVP/CBD 1:1 fiber at a magnification of 7,500 times. The scale bar is 1 μm.

Figure 15:
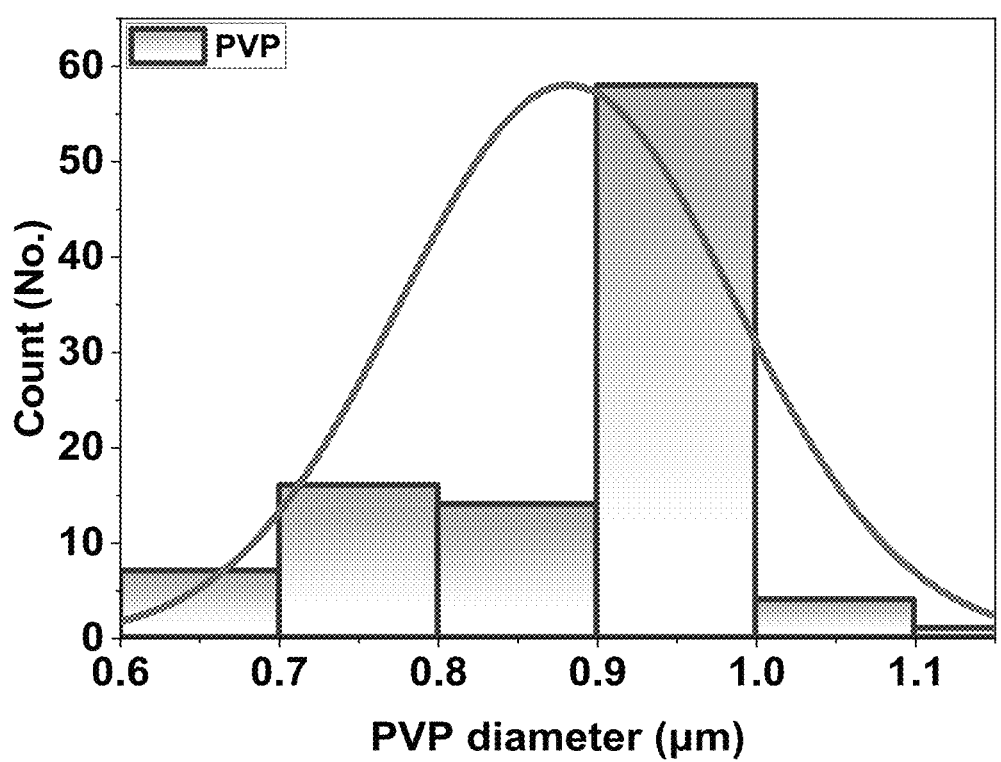

FIG. 15 shows a plot of count versus PVP diameter (in μm), showing a diameter distribution of PVP fibers.

Figure 16:
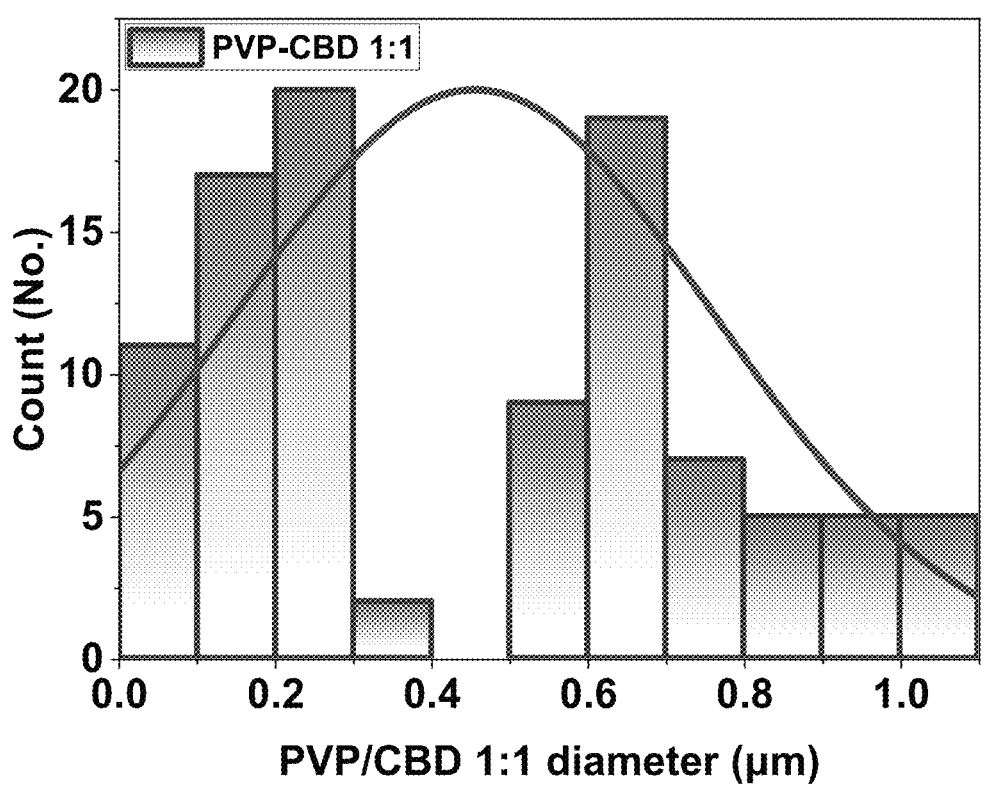

FIG. 16 shows a plot of count versus PVP/CBD 1:1 diameter (in μm), showing a diameter distribution of PVP/CBD 1:1 fibers.

Figure 17:

FIG. 17 shows a glove after 1 minute (min) of electrospinning of PVP/CBD 1:1 fiber.

Figure 18:
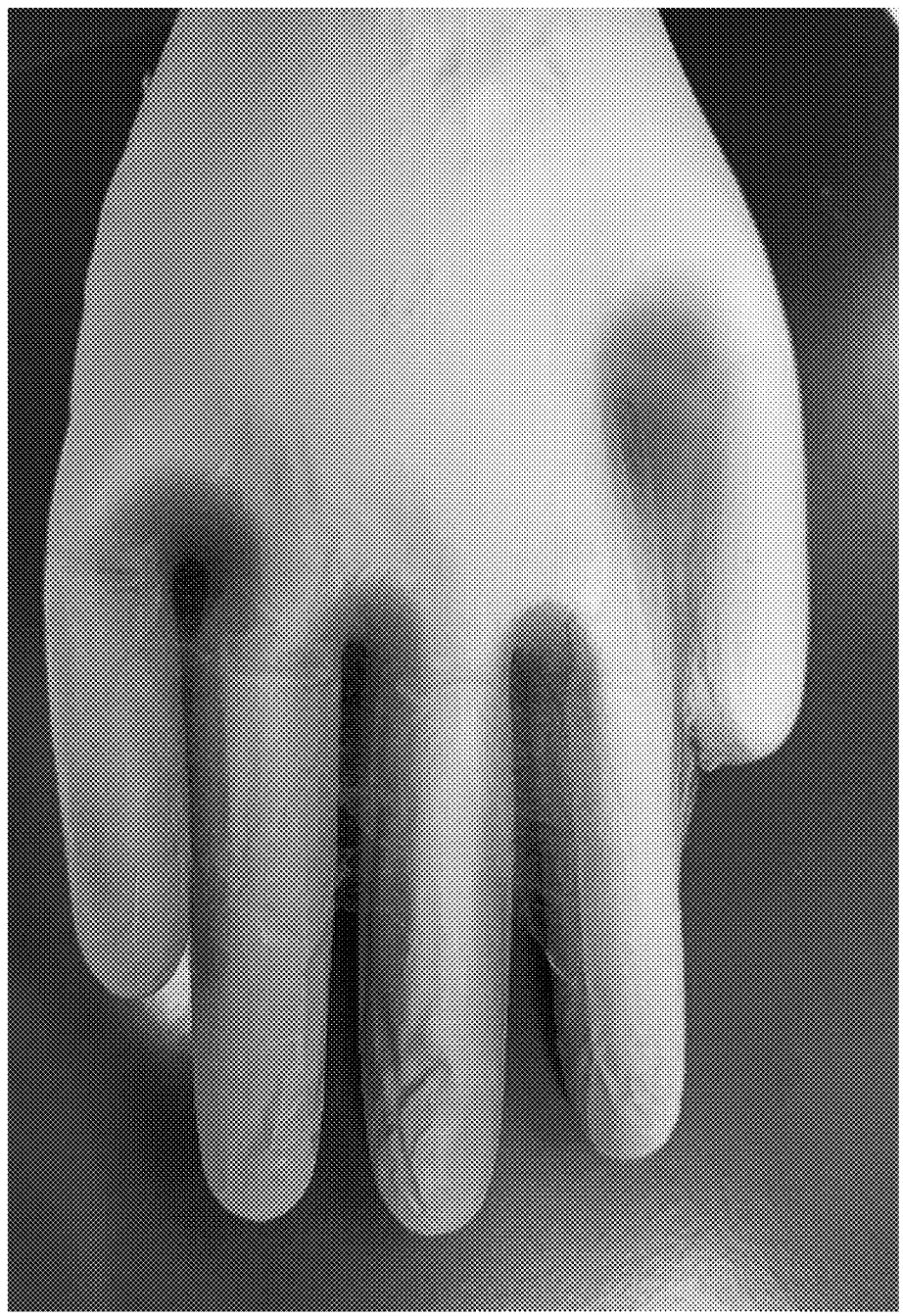

FIG. 18 shows a glove after 5 min of electrospinning of PVP/CBD 1:1 fiber.

Figure 19:
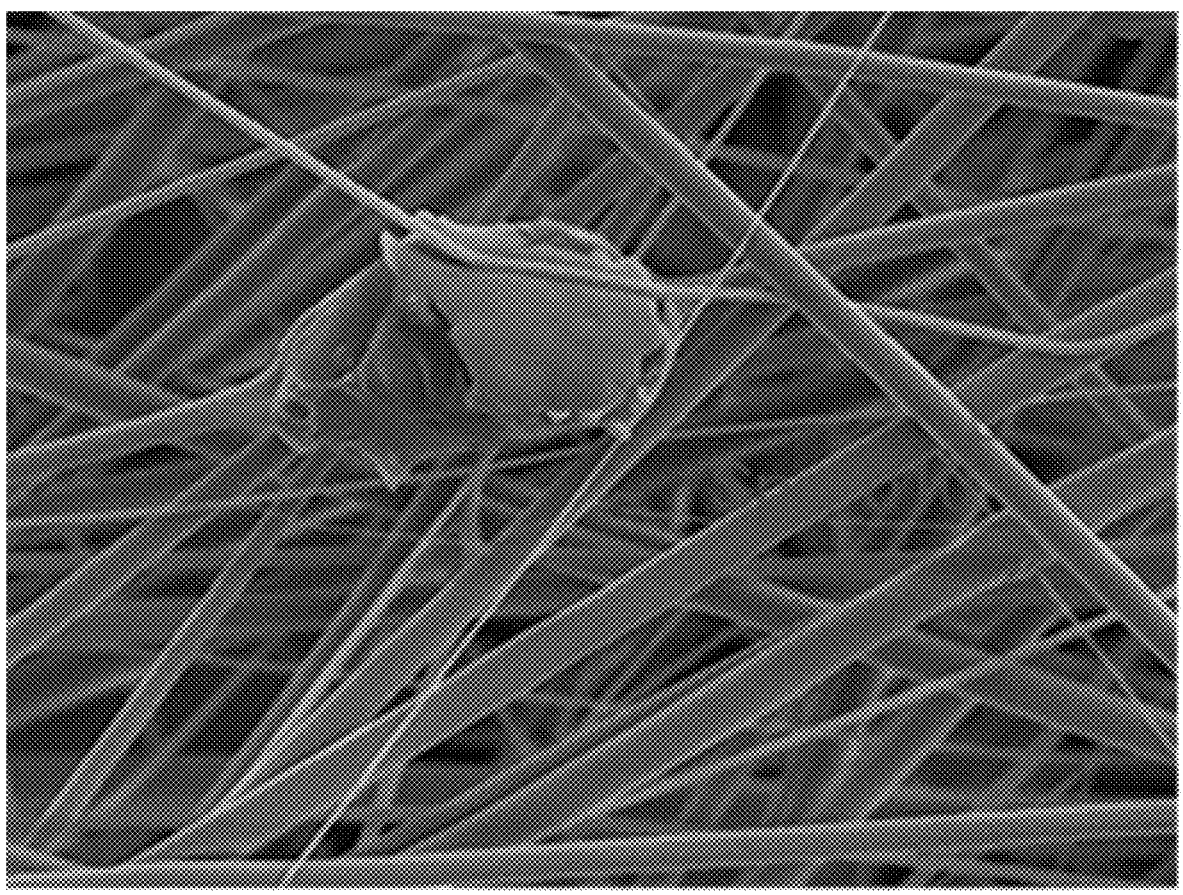

FIG. 19 shows a microscopic image with a location for an energy-dispersive X-ray spectroscopy (EDS) spectrum of a gold (Au)-coated PVP/CBD 1:1 uniform fiber. The plus sign (+) near the right side of the image and vertically near the middle marks the location.

Figure 20:
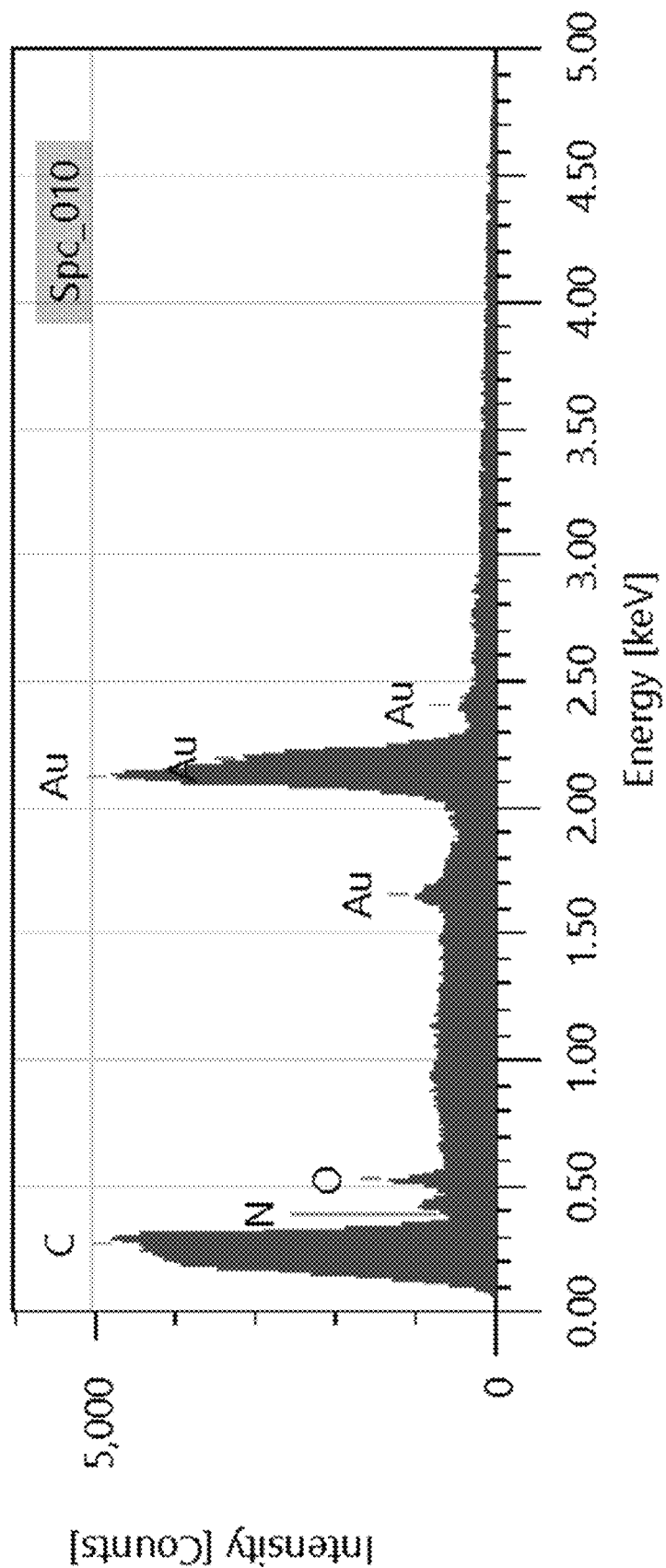

FIG. 20 shows the EDS spectrum of Au-coated PVP/CBD 1:1 uniform fiber, taken at the location marked in FIG. 19.

Figure 21:
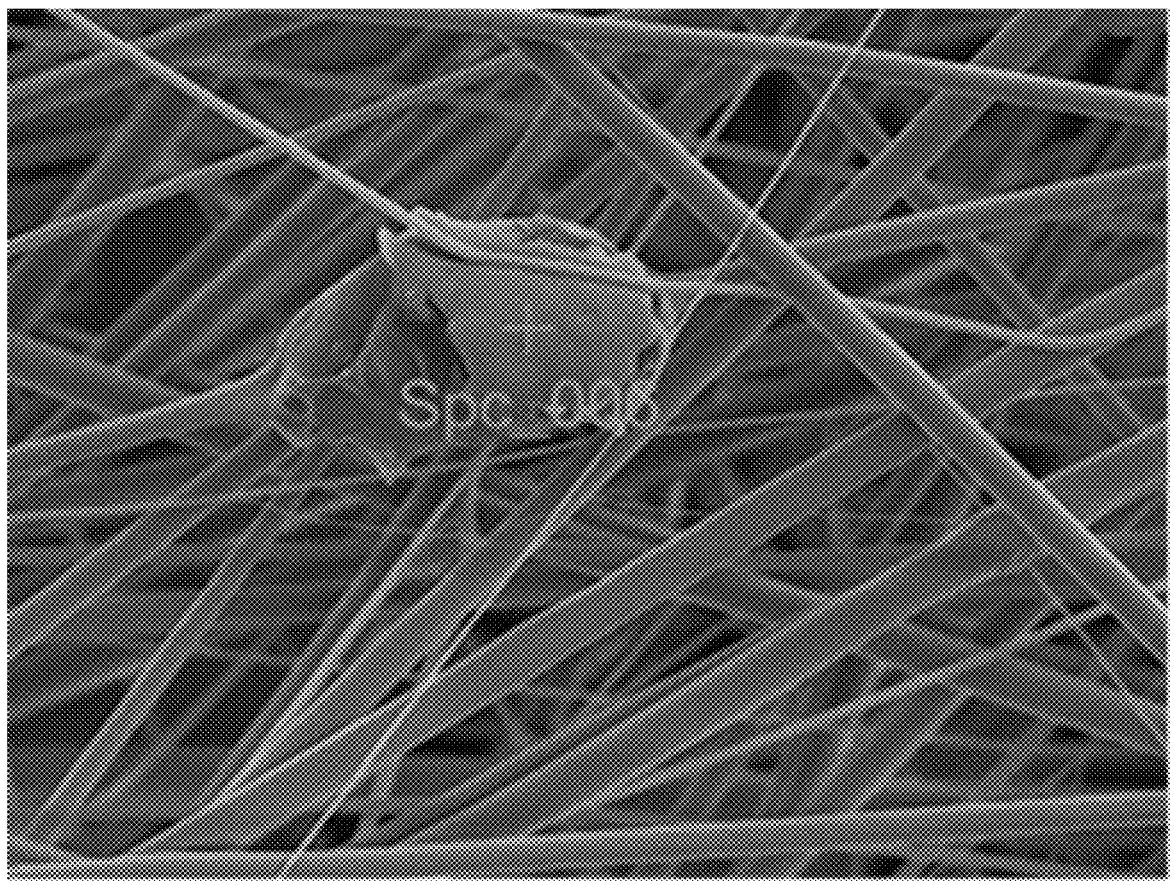

FIG. 21 shows a microscopic image with a location for an EDS spectrum of a large CBD particle on an Au-coated PVP/CBD 1:1 uniform fiber. The plus sign (+) near the center of the image marks the location.

Figure 22:
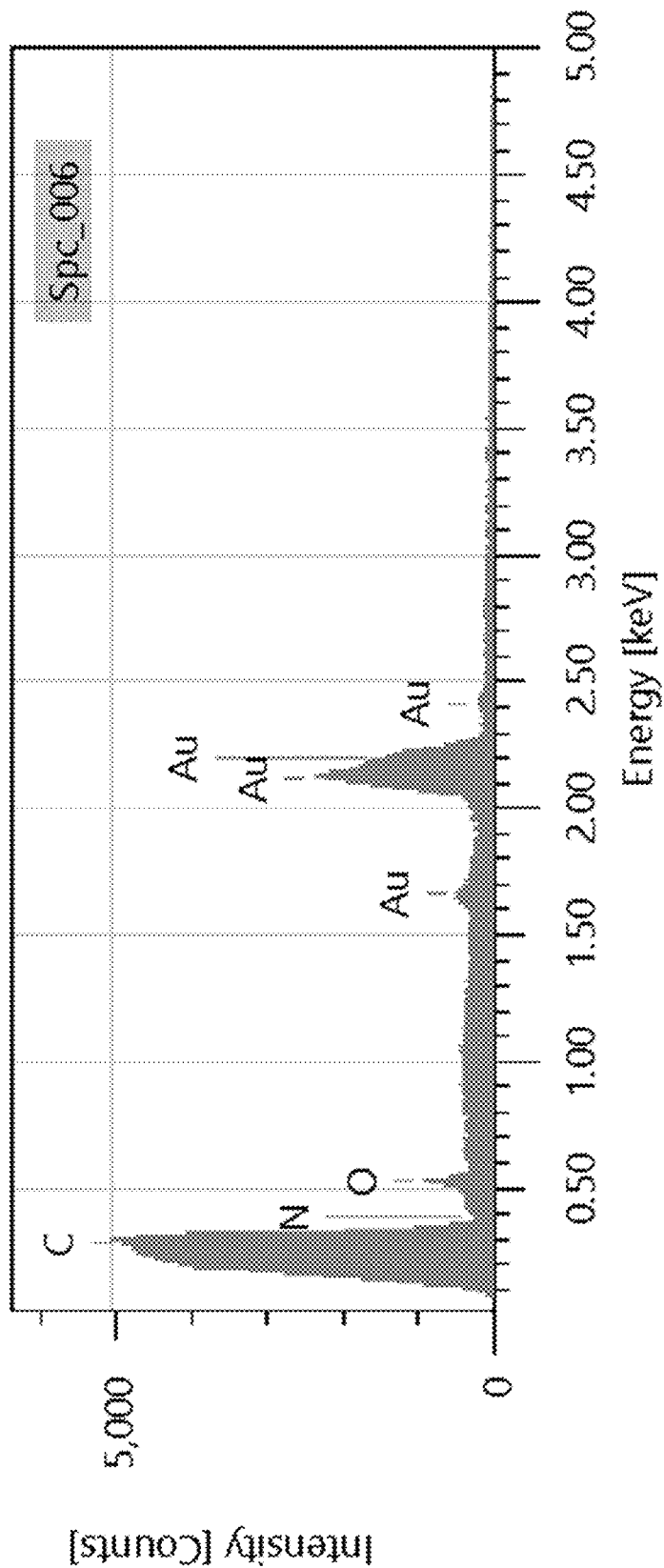

FIG. 22 shows the EDS spectrum of the large CBD particle on the Au-coated PVP/CBD 1:1 uniform fiber, taken at the location marked in FIG. 21.

Figure 23:
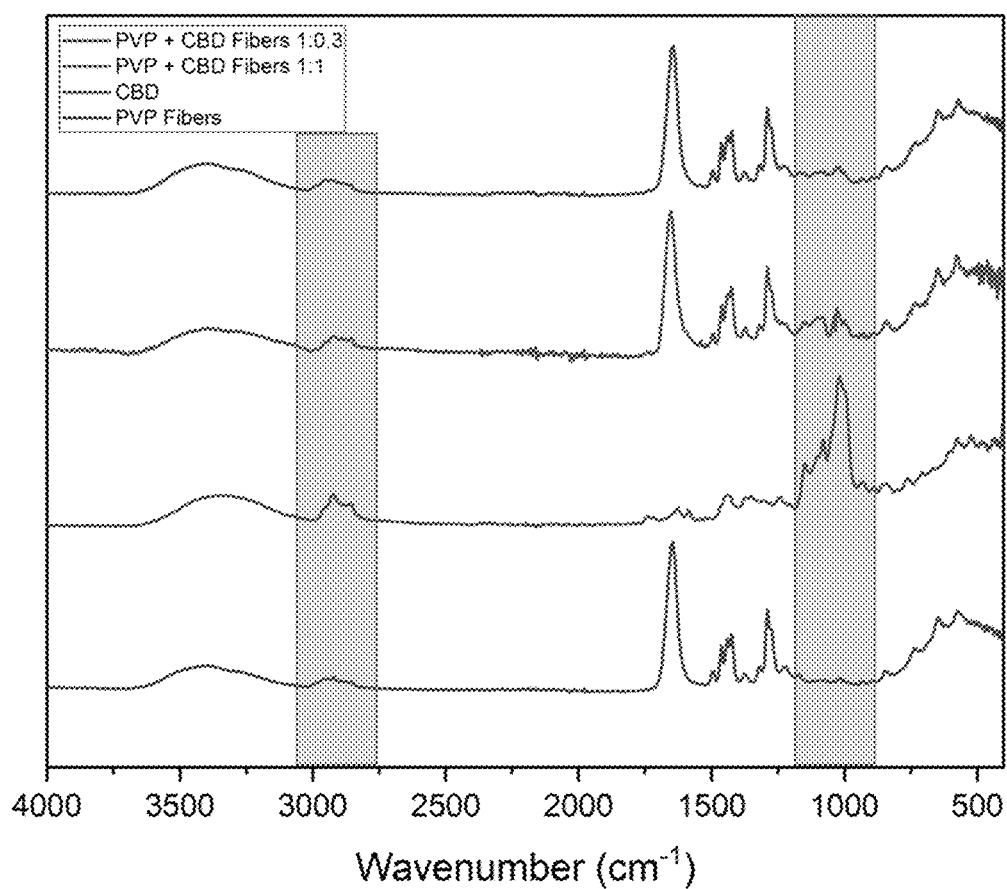

FIG. 23 shows Fourier transform infrared spectroscopy (FTIR) spectra (from 4000 per centimeter ($cm^{-1}$) to 400 $cm^{-1}$) of PVP fibers, CBD powder, PVP/CBD 1:0.3 (i.e., at a ratio of 1:0.3), and PVP/CBD 1:1. The uppermost (red) spectrum curve is for PVP/CBD 1:0.3; the (blue) spectrum curve that is second from the top is for PVP/CBD 1:1; the (green) spectrum curve that is second from the bottom is for CBD powder; and the lowermost (black) spectrum curve is for PVP fibers.

Figure 24:
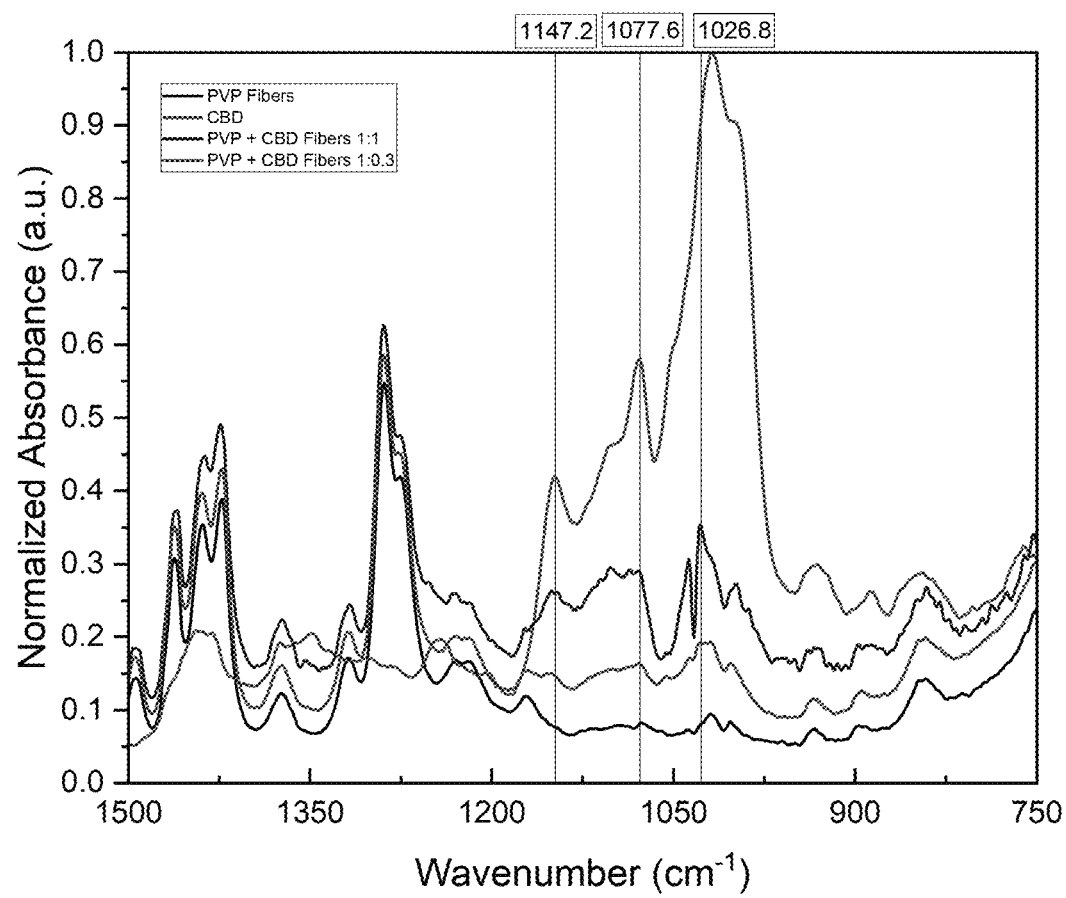

FIG. 24 shows FTIR spectra (from 1500 cm-1 to 750 $cm^{-1}$) of PVP fibers, CBD powder, PVP/CBD 1:0.3, and PVP/CBD 1:1. The plot has normalized absorbance (in arbitrary units (a.u.)) versus wavenumber (in $cm^{-1}$). The (green) spectrum curve with the highest normalized absorbance value at a wavenumber of 1050 $cm^{-1}$ is for CBD powder; the (blue) spectrum curve with the second-highest normalized absorbance value at a wavenumber of 1050 $cm^{-1}$ is for PVP/CBD 1:1; the (red) spectrum curve with the second-lowest normalized absorbance value at a wavenumber of 1050 $cm^{-1}$ is for PVP/CBD 1:0.3; and the (black) spectrum curve with the lowest normalized absorbance value at a wavenumber of 1050 $cm^{-1}$ is for PVP fibers.

Figure 25:
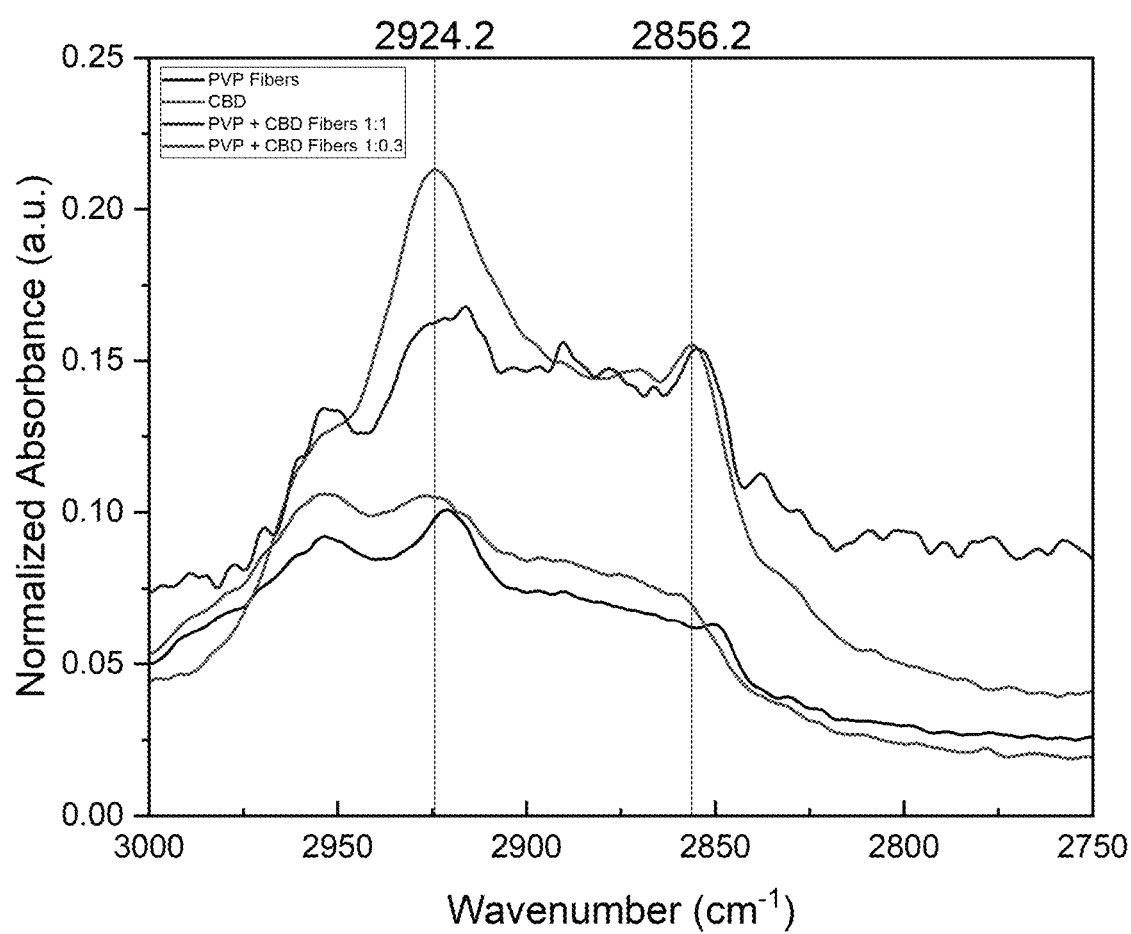

FIG. 25 shows FTIR spectra (from 3000 cm-1 to 2750 $cm^{-1}$) of PVP fibers, CBD powder, PVP/CBD 1:0.3, and PVP/CBD 1:1. The plot has normalized absorbance (in a.u.) versus wavenumber (in $cm^{-1}$). The (green) spectrum curve with the highest normalized absorbance value at a wavenumber of 2925 $cm^{-1}$ is for CBD powder; the (blue) spectrum curve with the second-highest normalized absorbance value at a wavenumber of 2925 $cm^{-1}$ is for PVP/CBD 1:1; the (red) spectrum curve with the second-lowest normalized absorbance value at a wavenumber of 2925 $cm^{-1}$ is for PVP/CBD 1:0.3; and the (black) spectrum curve with the lowest normalized absorbance value at a wavenumber of 2925 $cm^{-1}$ is for PVP fibers.

Figure 26:
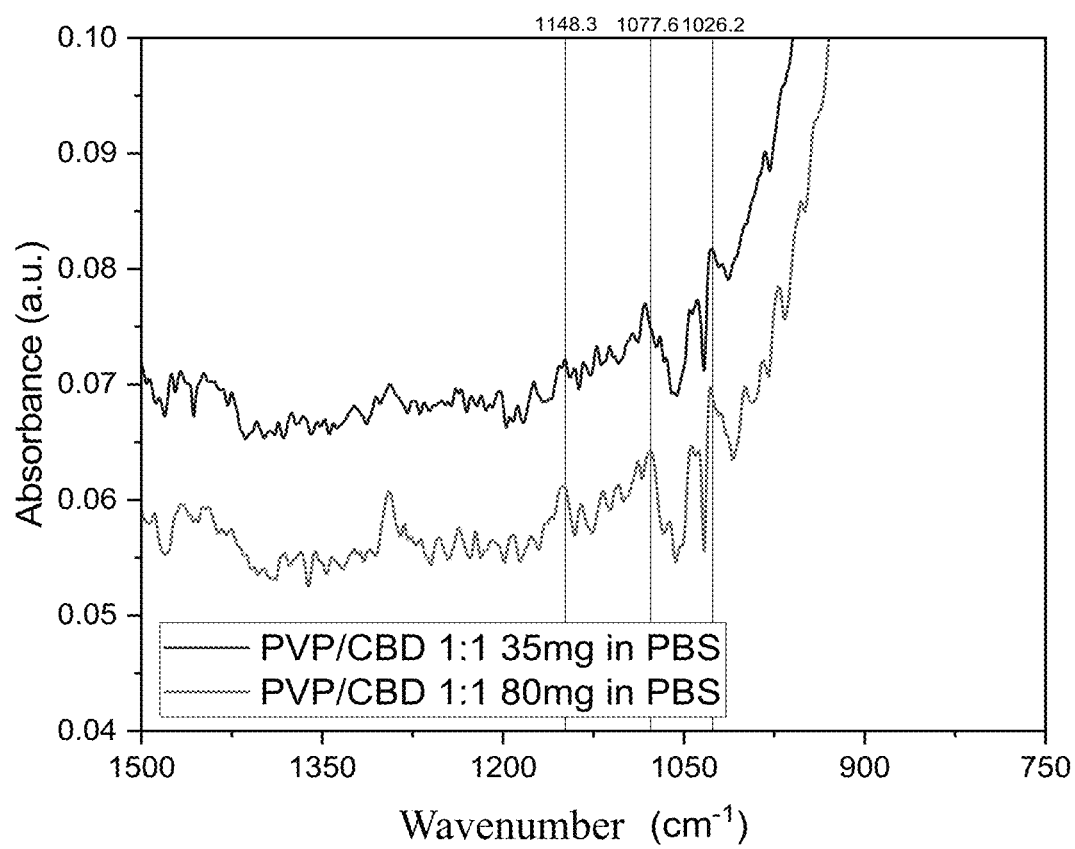

FIG. 26 shows FTIR spectra (from 1500 cm-1 to 750 $cm^{-1}$) of 35 milligrams (mg) of PVP/CBD 1:1 fiber drug release in phosphate-buffered saline (PBS) solution and 80 mg of PVP/CBD 1:1 fiber drug release in PBS solution. The plot has absorbance (in a.u.) versus wavenumber (in $cm^{-1}$). The (blue) spectrum curve with the higher absorbance values is for the 35 mg; and the (red) spectrum curve with the lower absorbance values is for the 80 mg.

Figure 27:
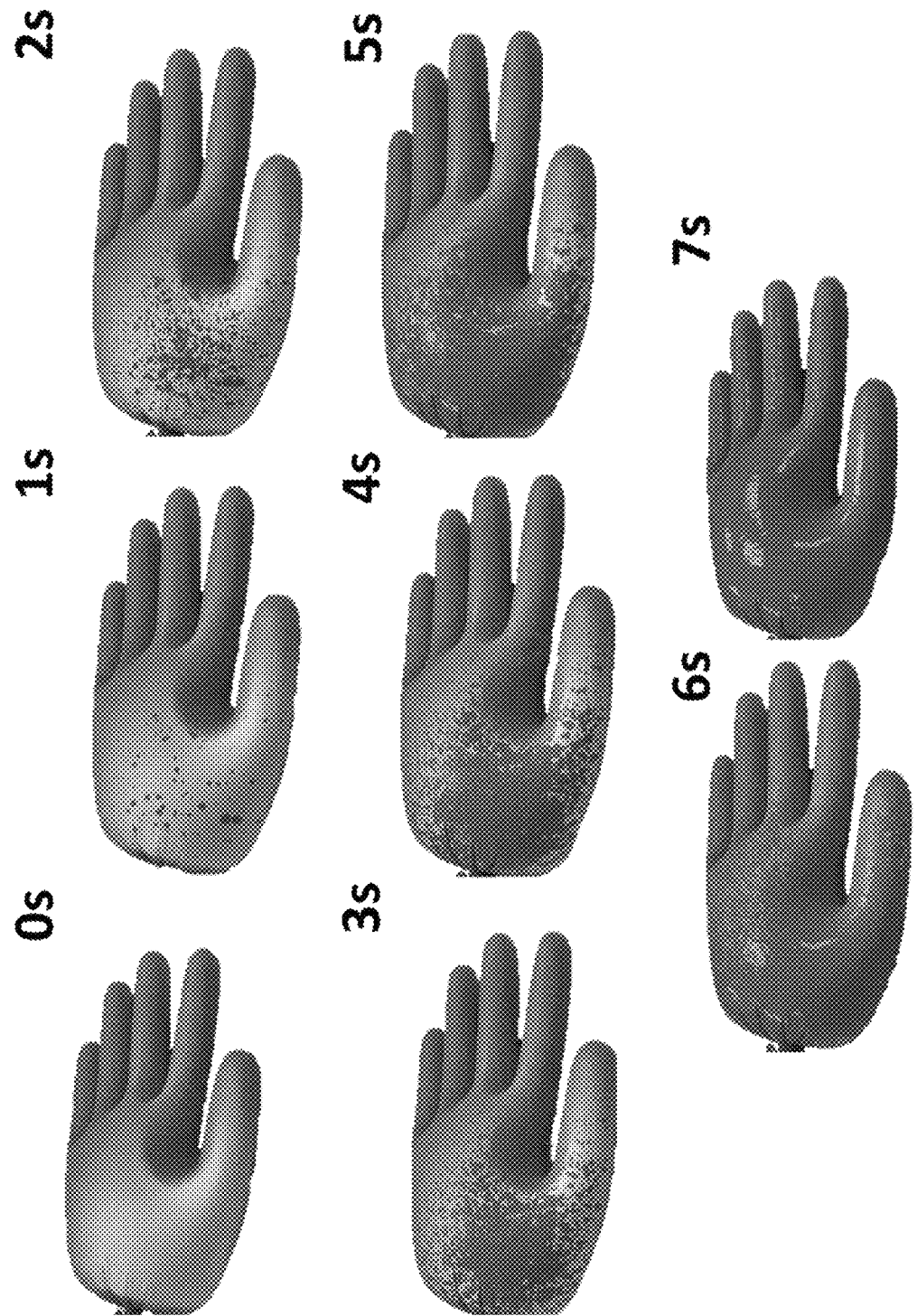

FIG. 27 shows images at different times of rapid drug delivery testing on a glove with 1 min of PVP/CBD 1:1 fiber electrospinning. The images are shown after 0 seconds(s), 1 s, 2 s, 3 s, 4 s, 5 s, 6 s, and 7 s, as labeled in FIG. 27.

Figure 28:

FIG. 28 shows a 3D view of a wearable, ultralow power, and needleless electrospinning device, according to an embodiment of the subject invention. FIG. 28 shows the lower surface of the device.

Figure 29:
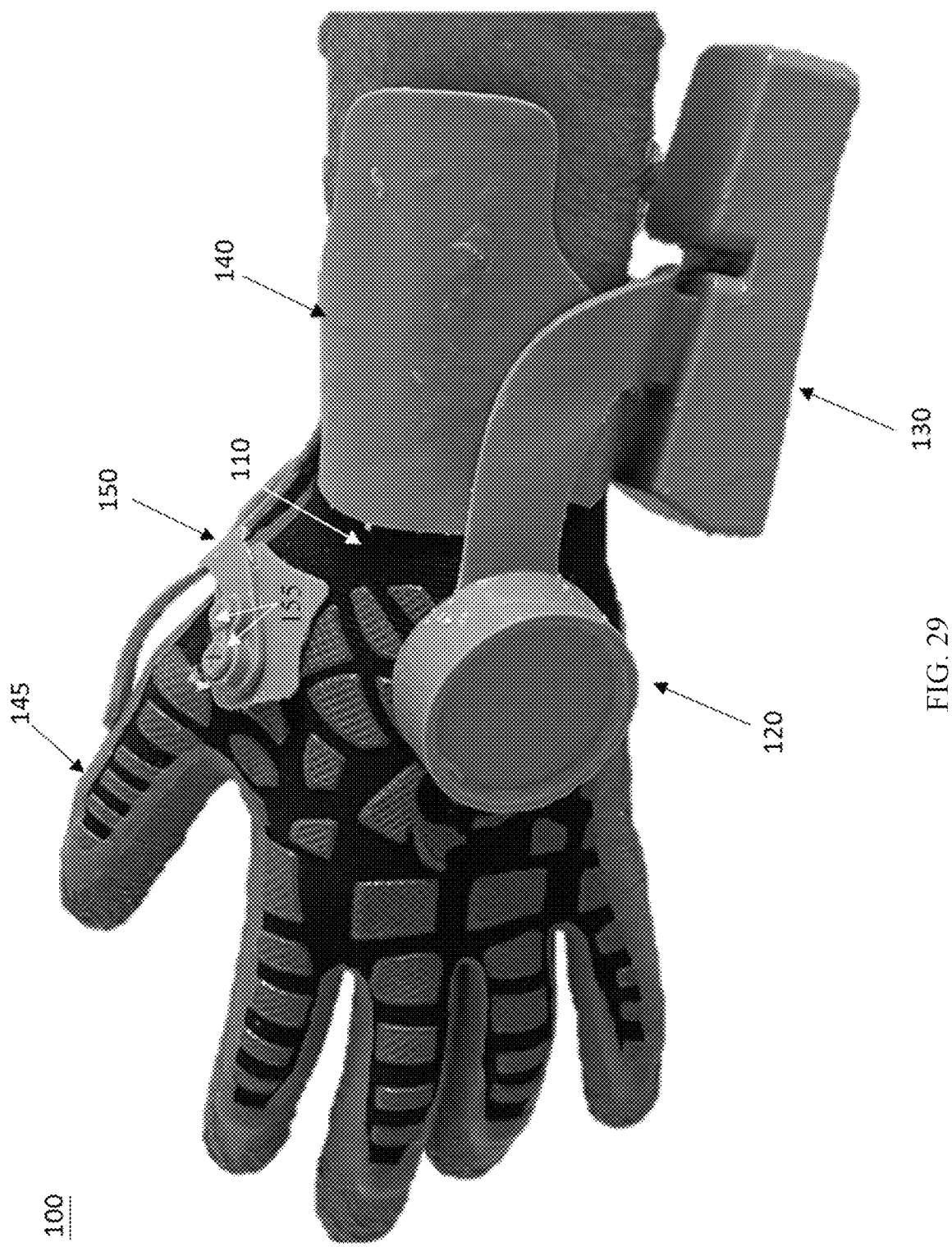

FIG. 29 shows a 3D view of a wearable, ultralow power, and needleless electrospinning device, according to an embodiment of the subject invention. FIG. 29 shows the upper surface of the device.

Figure 30:
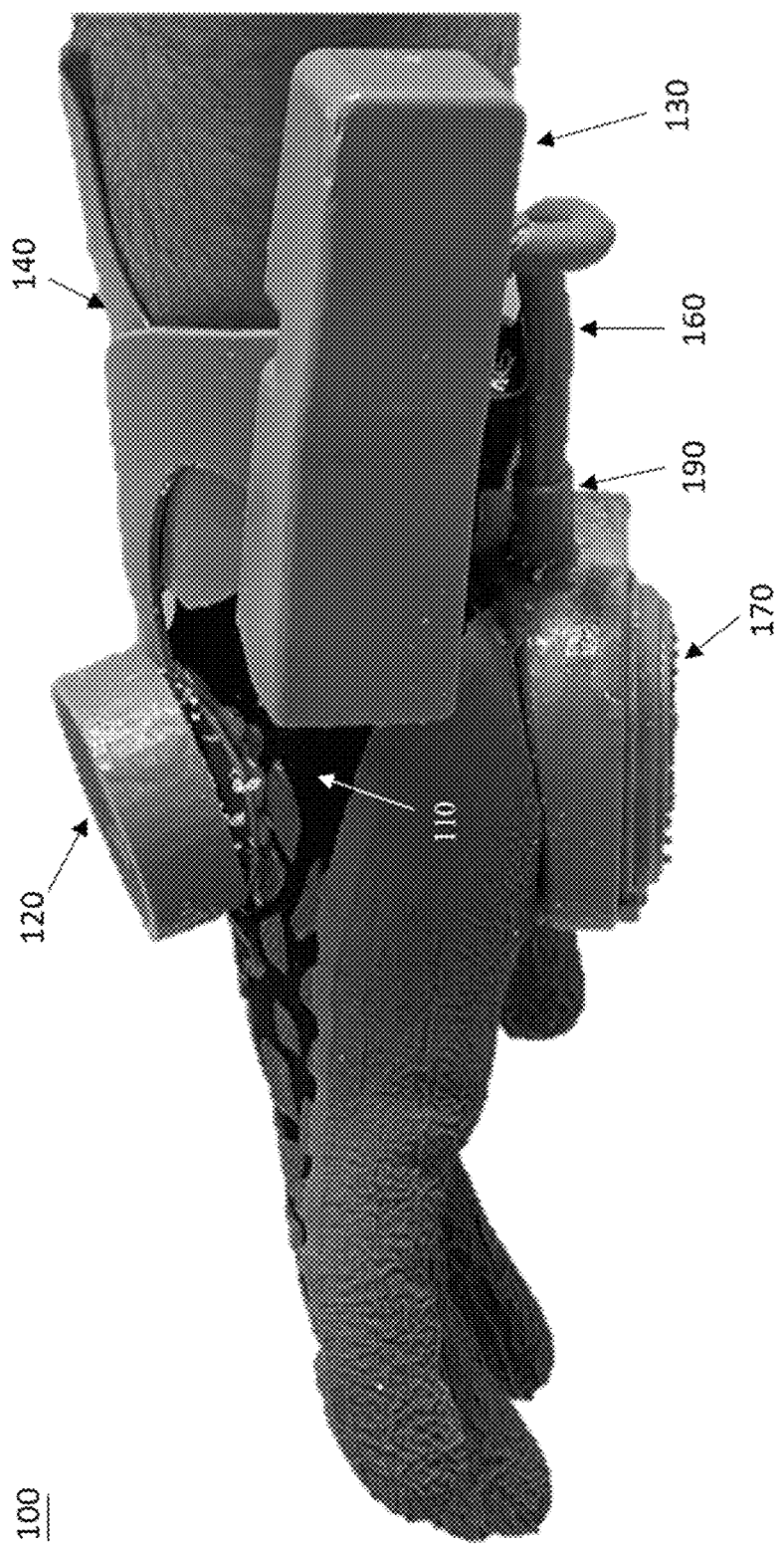

FIG. 30 shows a 3D view of a wearable, ultralow power, and needleless electrospinning device, according to an embodiment of the subject invention. FIG. 30 shows a side surface of the device.

Figure 31:
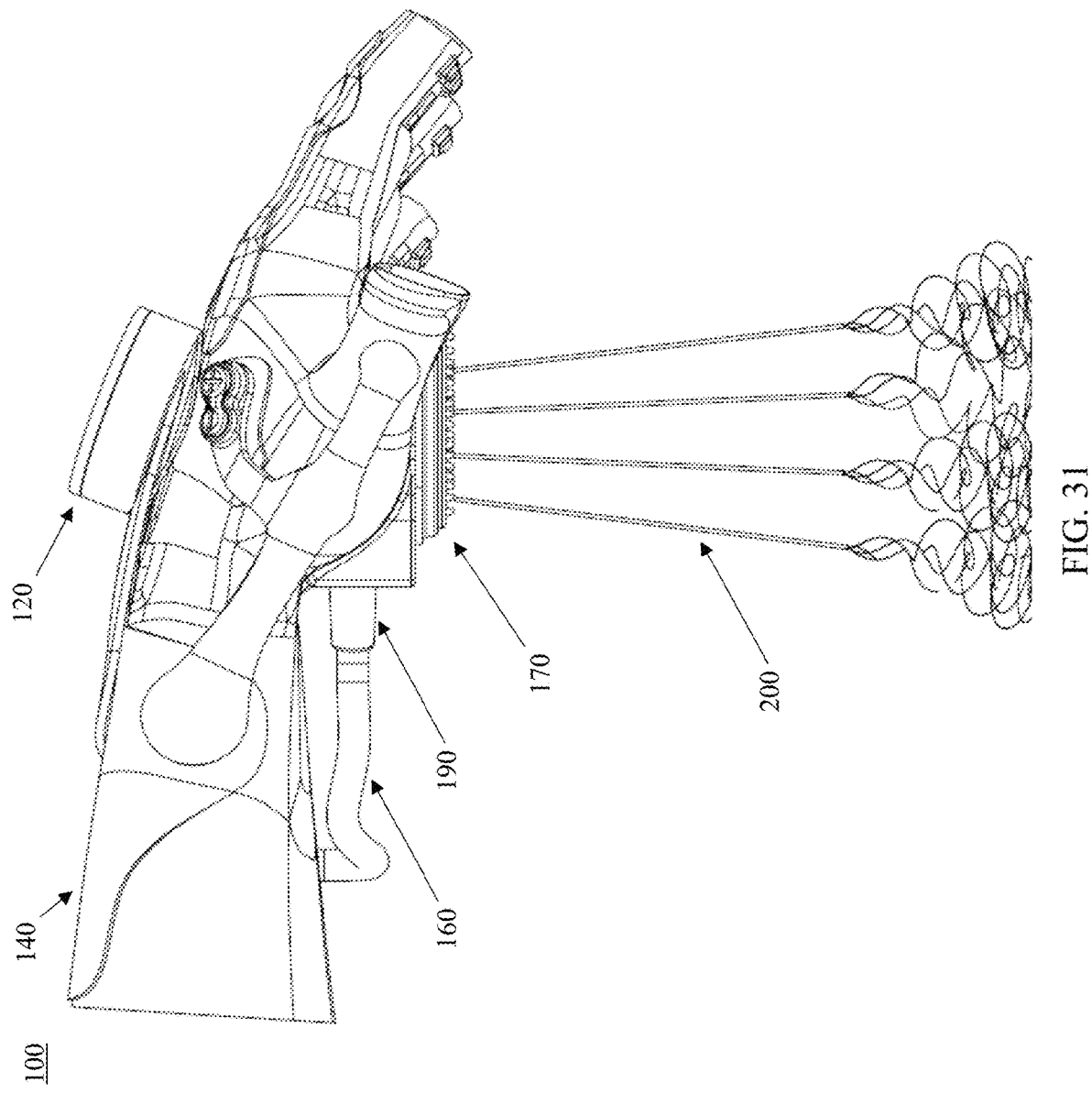

FIG. 31 shows a view of a wearable, ultralow power, and needleless electrospinning device, according to an embodiment of the subject invention. This figure shows the electrospinning process using a 4-nozzle needless spinneret for the electrospinning device. The smoke-like regions below the nozzles are nanofiber jets and bundles.

Figure 32:
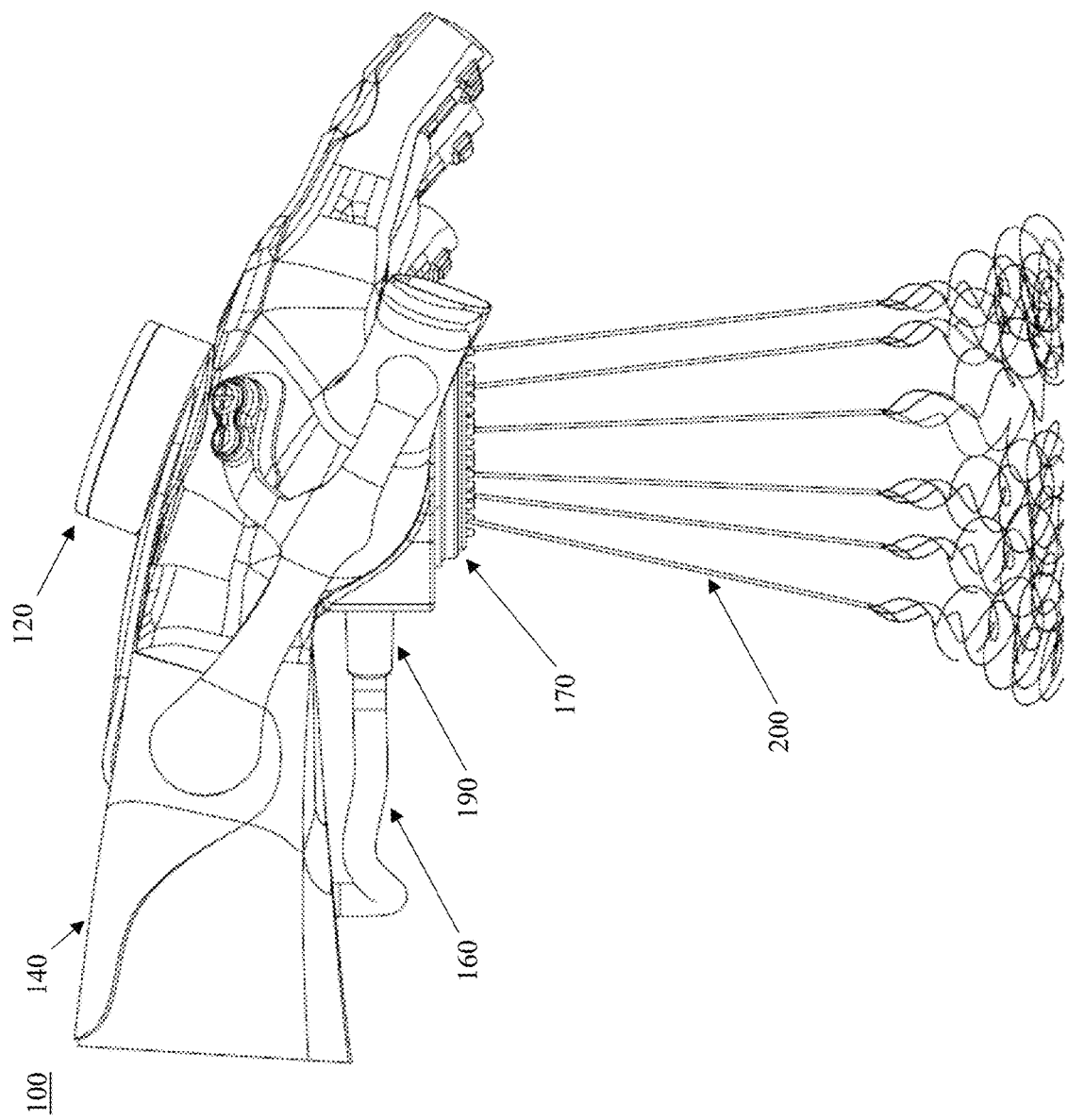

FIG. 32 shows a view of a wearable, ultralow power, and needleless electrospinning device, according to an embodiment of the subject invention. This figure shows the electrospinning process using a 6-nozzle needless spinneret for the electrospinning device. The smoke-like regions below the nozzles are nanofiber jets and bundles.

DETAILED DESCRIPTION

Embodiments of the subject invention provide novel and advantageous devices and methods for nanofiber-based membrane fabrication. Portable (e.g., handheld) electrostatic spinning or electrospinning devices can be used for nanofiber-based membrane fabrication (e.g., wound care films or membranes, such as cannabidiol (CBD)-loaded films or membranes) and can be needleless, wearable, and/or ultralow power.

The limitations of current devices for producing fiber-based membranes or films include high input power, low drug loading rate, inconsistent fiber quality, safety issues due to high output voltages, and limited scalability. In order to address these limitations, embodiments of the subject invention provide ultralow power (e.g., 1.4 Volts (V) or less, such as 1 V or less) battery-operated and hand-wearable electrospinning devices having a novel needleless spinneret. The devices are capable of fabricating (and configured to fabricate) drug-loaded fiber-based thin films or membranes. For example, CBD-loaded fiber-based products can be fabricated and/or designed. The functions of the fiber-based products but are not limited to pain relief, anti-inflammation, and wound healing.

FIGS. 1-6 show views of a wearable, ultralow power, and needleless electrospinning device, according to an embodiment of the subject invention. FIGS. 28-30 show images of a wearable, ultralow power, and needleless electrospinning device, according to an embodiment, which has been fabricated using three-dimensional (3D) printing. Referring to FIGS. 1-6 and 28-30, the device 100 can include an isolating (and/or insulating) wearable glove 110, a solution delivery unit 130, a wrist support 140, a needleless spinneret 170 (which may be referred to as a needleless spinneret reservoir), a solution delivery conduit 160 connecting the solution delivery unit 130 to the needleless spinneret 170, a needleless spinneret fluid delivery coupler 190 coupling the solution delivery conduit 160 to the needleless spinneret 170, and a solution flow control 120 used to control the solution flowing (e.g., flow rate and/or amount provided) from the solution delivery unit 130 to the needleless spinneret 170. The solution delivery unit 130 can have the solution stored therein that will be provided to the needleless spinneret 170 for fabricating the nanofiber-based membranes or films. For example, the solution can be a drug-loaded (e.g., CBD-loaded) bulk material solution. The bulk material is capable of being electrospun (e.g., a polymer, such as polyvinylpyrrolidone (PVP)). The drug(s) and/or bulk material(s) can be dissolved in one or more solvents (e.g., phosphate-buffered saline (PBS) solution). The needleless spinneret 170 can be disposed on a lower surface of the glove 110 (i.e., the surface that will be up against the palm of the user's hand during use). The solution flow control 120 can be disposed on an upper surface of the glove 110 (i.e., the surface that will be up against the back of the user's hand during use). The solution delivery unit 130 can be disposed on a side surface (e.g., an outer side surface (i.e., the left side surface a left-hand glove when viewed from above or the right side surface of a right-hand glove when viewed from above)) of the glove 110. The wrist support 140 can be disposed on the upper surface, the lower surface, the outer side surface, and/or the inner side surface of the glove 110. The glove 110 can extend and include material for the fingertips of the user (see, e.g., FIGS. 28-30) or can extend only partially along the fingers and be cut off before reaching the fingertips (see, e.g., FIGS. 1-6). The glove 110 material can be insulating (i.e., electrically and/or thermally insulating).

The device 100 can further include a rigid side portion 150, which may have a voltage control 155 disposed thereon. The voltage control 155 can include at least one terminal (e.g., a positive terminal and a negative terminal) and/or can either comprise a battery or can be configured to connect to one or more batteries. The rigid side portion 150 can be disposed on, for example, and inner side surface (i.e., the right side surface a left-hand glove when viewed from above or the left side surface of a right-hand glove when viewed from above). The voltage control 155 can be in operable communication with the needleless spinneret 170, the solution delivery unit 130, and/or the solution flow control 120. The voltage control 155 can be or can include, for example, a low voltage battery (e.g., 1.4 V or less, such as 1 V or less, 0.8 V or less, or 0.5 V or less). The solution flow control 120 can be in operable communication with the solution delivery unit 130, and a user can control the solution flowing (e.g., flow rate and/or amount provided) from the solution delivery unit 130 to the needleless spinneret 170 by using the solution flow control 120. For example, a knob or other device can be turned, or a touch screen can be used. In the latter case, the solution flow control 120 and/or the solution delivery unit 130 can have electronics (e.g., circuit board(s)) included therein.

The device 100 can also include one or more lights 180, which can be used to illuminate the target site (e.g., a wound site, a pain site, a site of inflammation, or another site on a patient) during use. The lights 180 can be in operable communication with the voltage control 155. The lights 180 can alternatively (or additionally) have their own battery or batteries to provide power to the lights 180. For example, each light 180 can have its own battery, one battery can be used for all lights 180, some or all lights can be powered by the voltage control 155, or some combination thereof. The lights 180 can be, for example, light emitting diodes (LEDs), though embodiments are not limited thereto. The lights 180 can be disposed on, for example, the bottom surface of the device 100 (e.g., near the end of the glove material 110).

Any or all of the elements (120, 130, 140, 150, 160, 170, 180, 190) can be attached to the glove 110, for example via one or more adhesives and/or via suitable mechanical means (e.g., a fastener).

Figure 1:
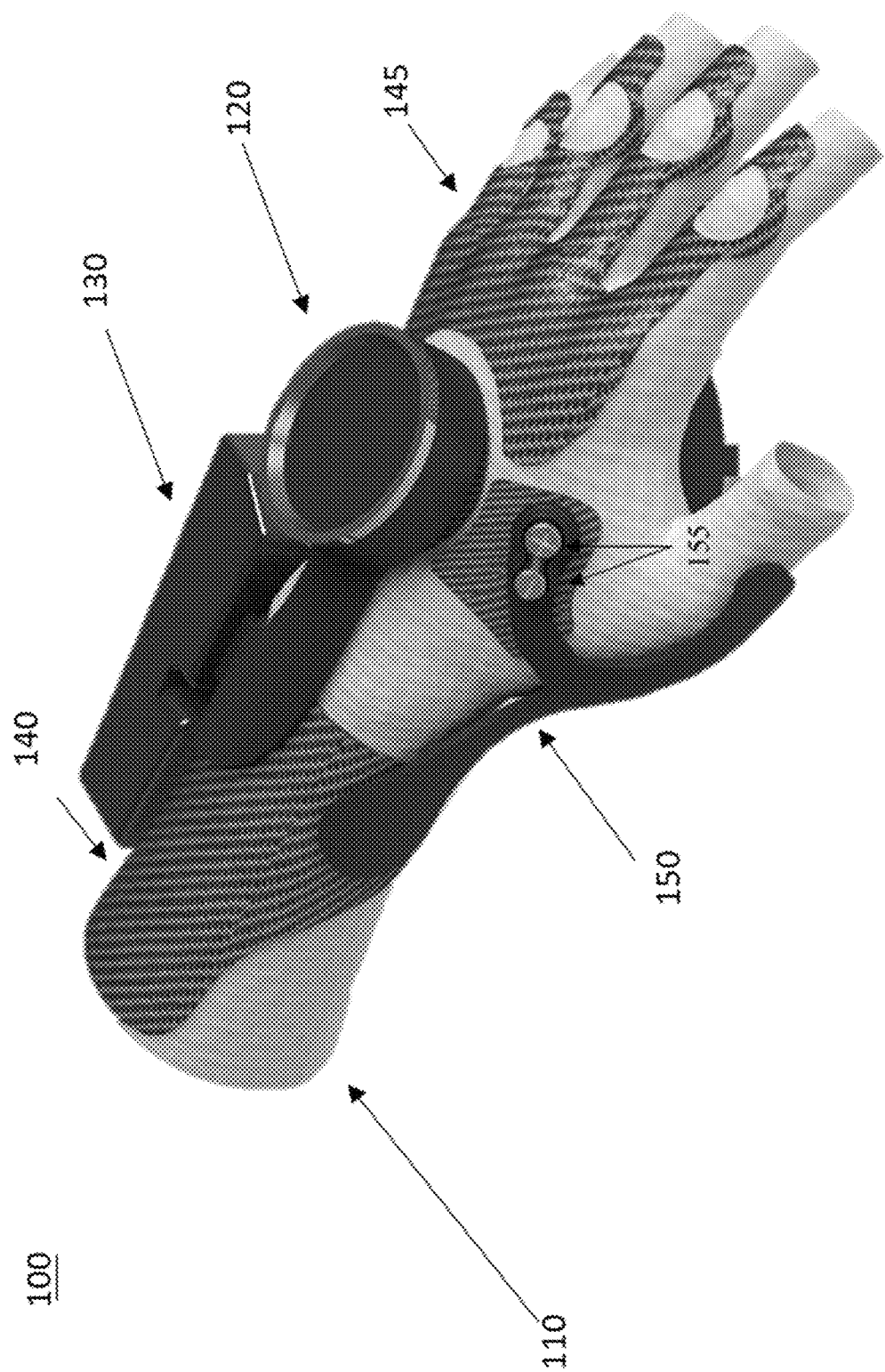
FIG. 1 shows a three-dimensional (3D) view of a wearable, ultralow power, and needleless electrospinning device, according to an embodiment of the subject invention.
Figure 2:
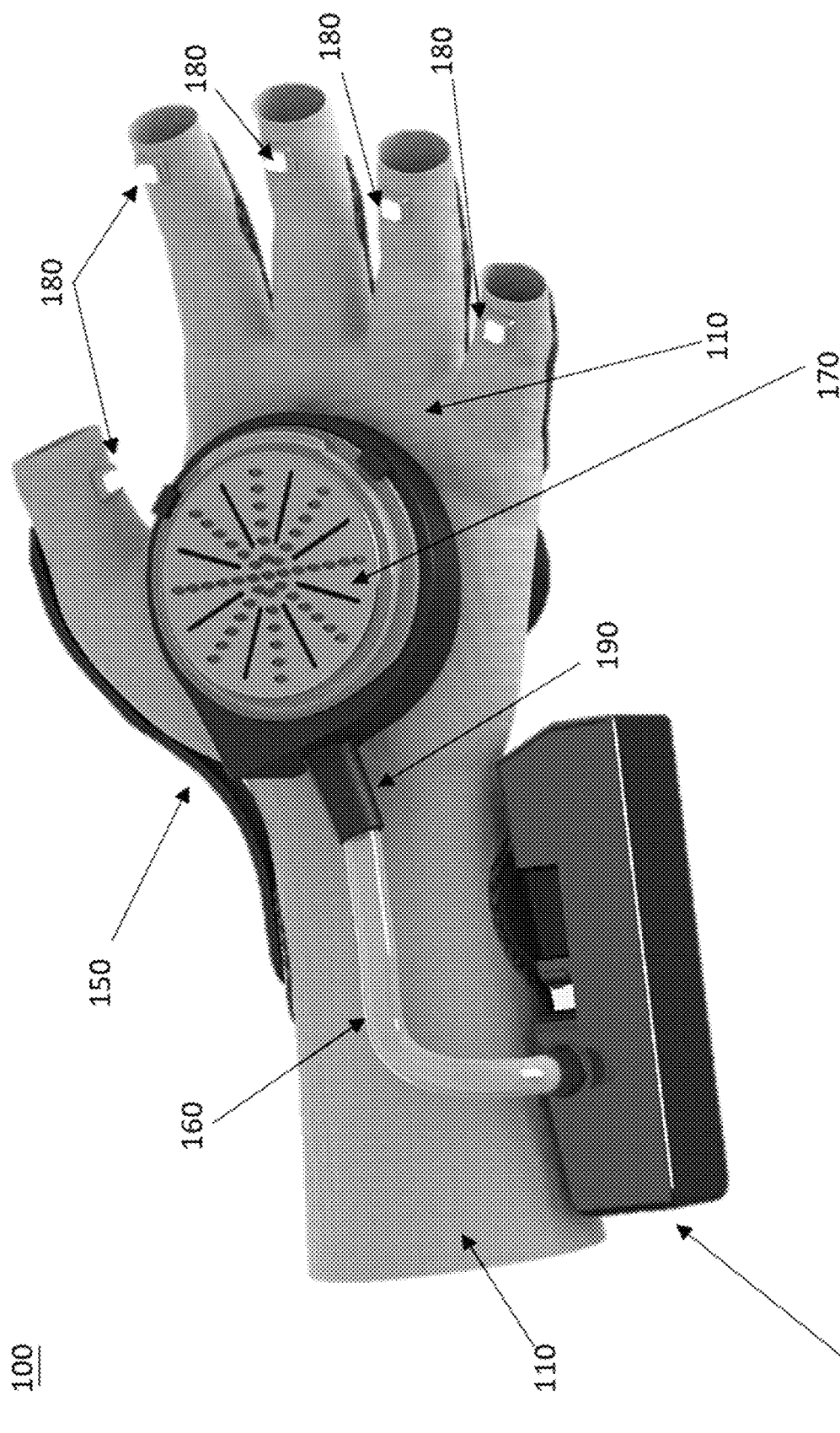
FIG. 2 shows a 3D view of a wearable, ultralow power, and needleless electrospinning device, according to an embodiment of the subject invention.
Figure 3:
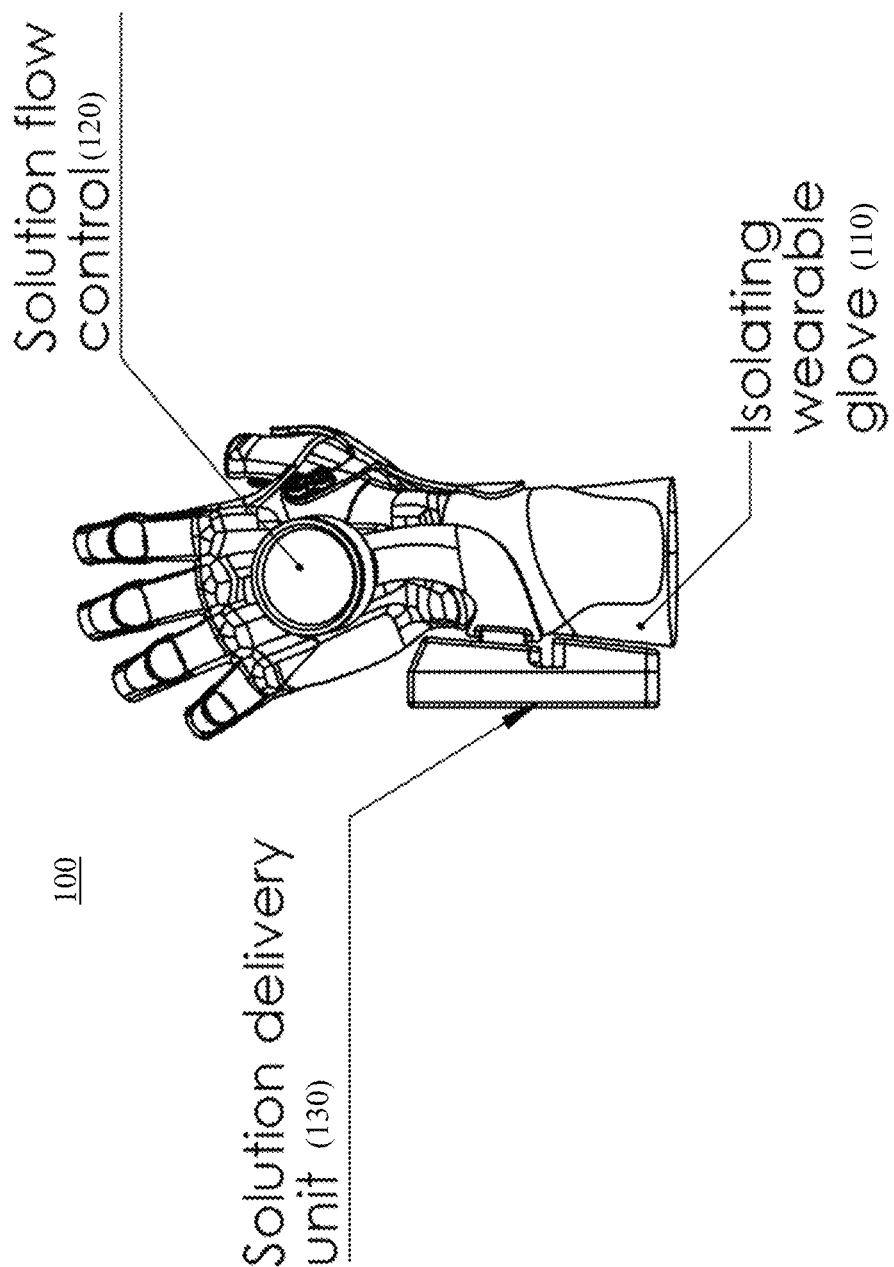
FIG. 3 shows a top view of a wearable, ultralow power, and needleless electrospinning device, according to an embodiment of the subject invention.
Figure 4:
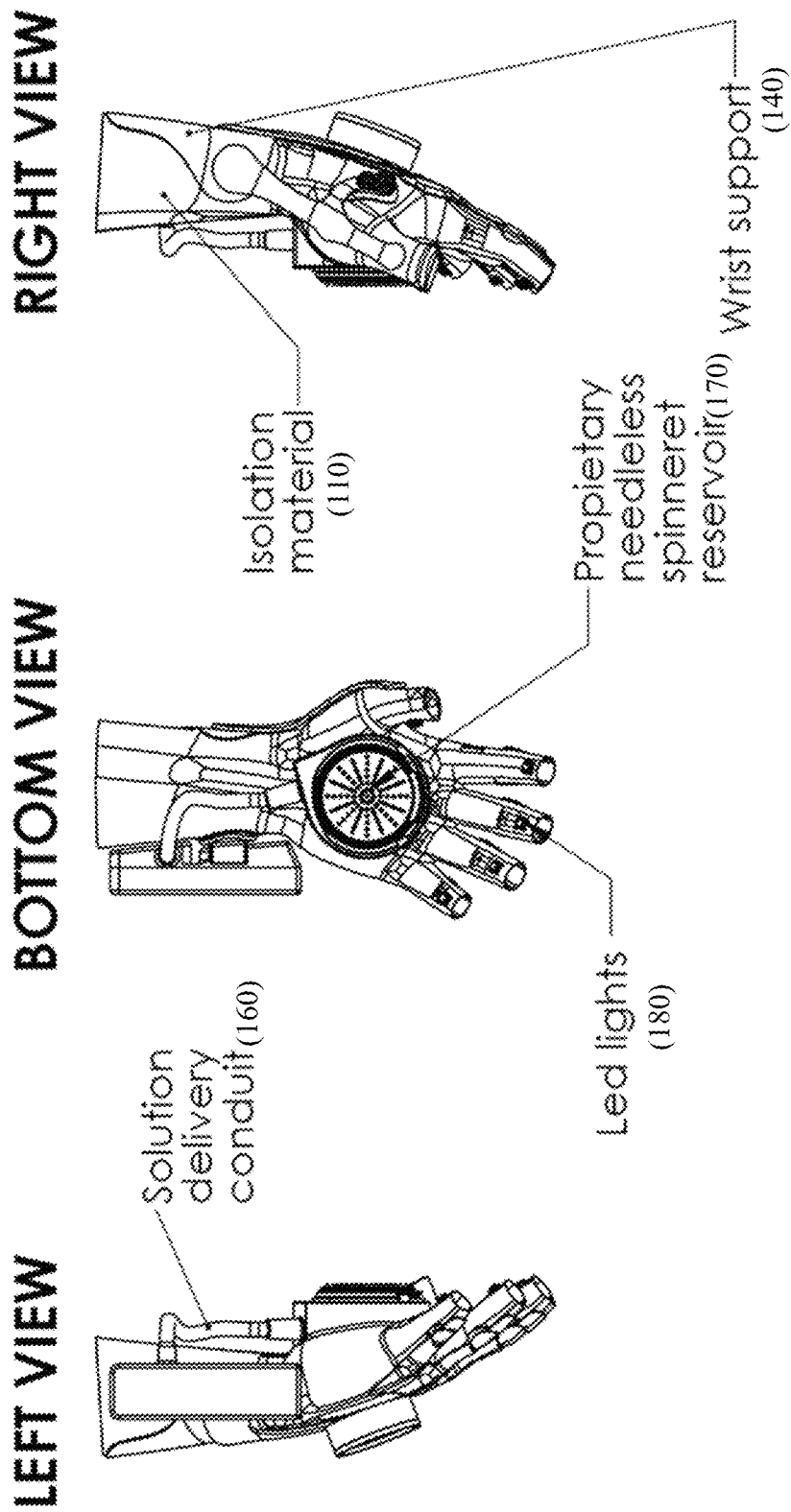
FIG. 4 shows a left view (left-most portion of FIG. 4), a bottom view (middle portion of FIG. 4), and a right view (right-most portion of FIG. 4) of a wearable, ultralow power, and needleless electrospinning device, according to an embodiment of the subject invention.
Figure 5:
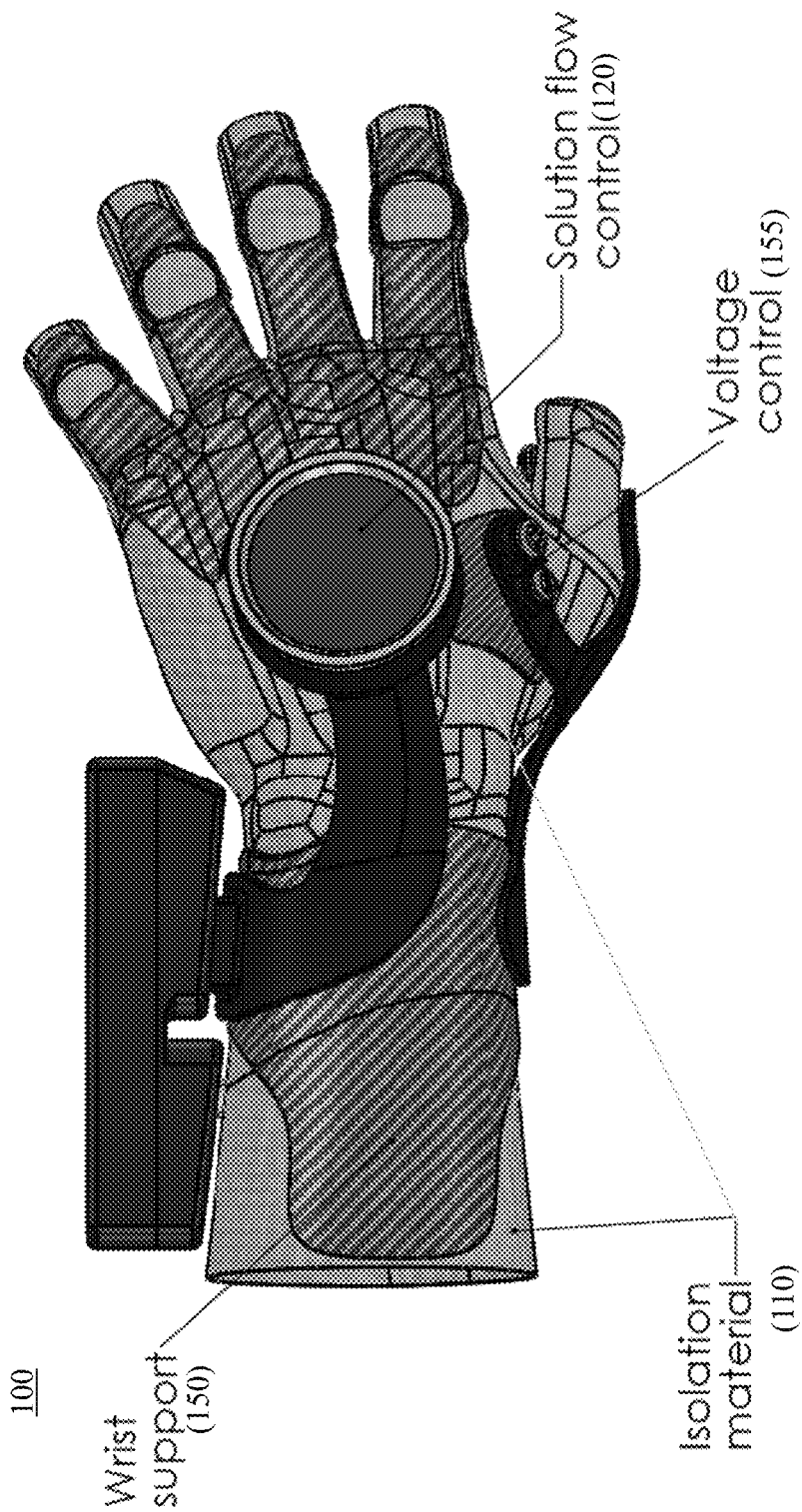
FIG. 5 shows a top view of a wearable, ultralow power, and needleless electrospinning device, according to an embodiment of the subject invention.
Figure 6:
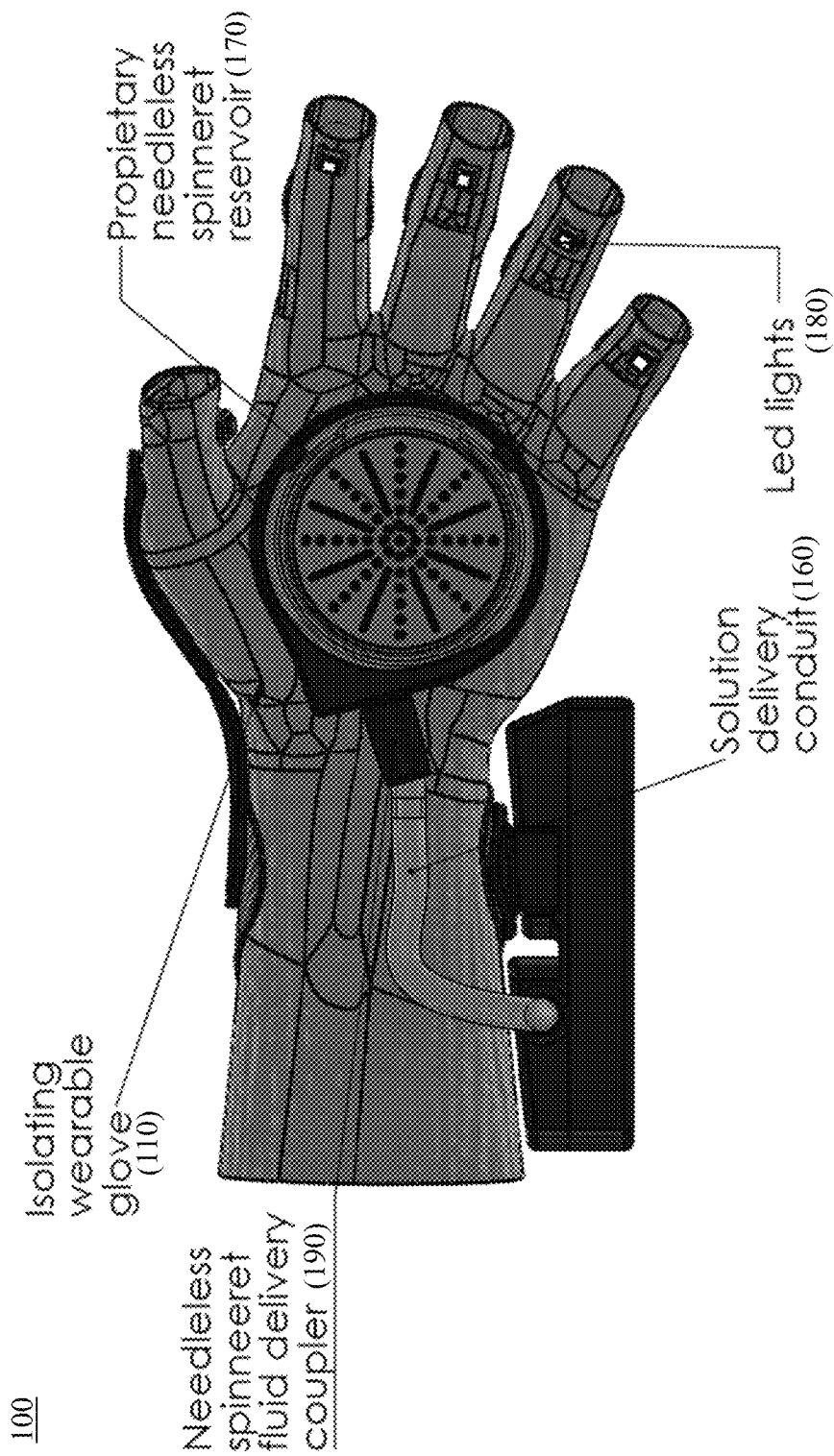
FIG. 6 shows a top view of a wearable, ultralow power, and needleless electrospinning device, according to an embodiment of the subject invention.
Figure 8:
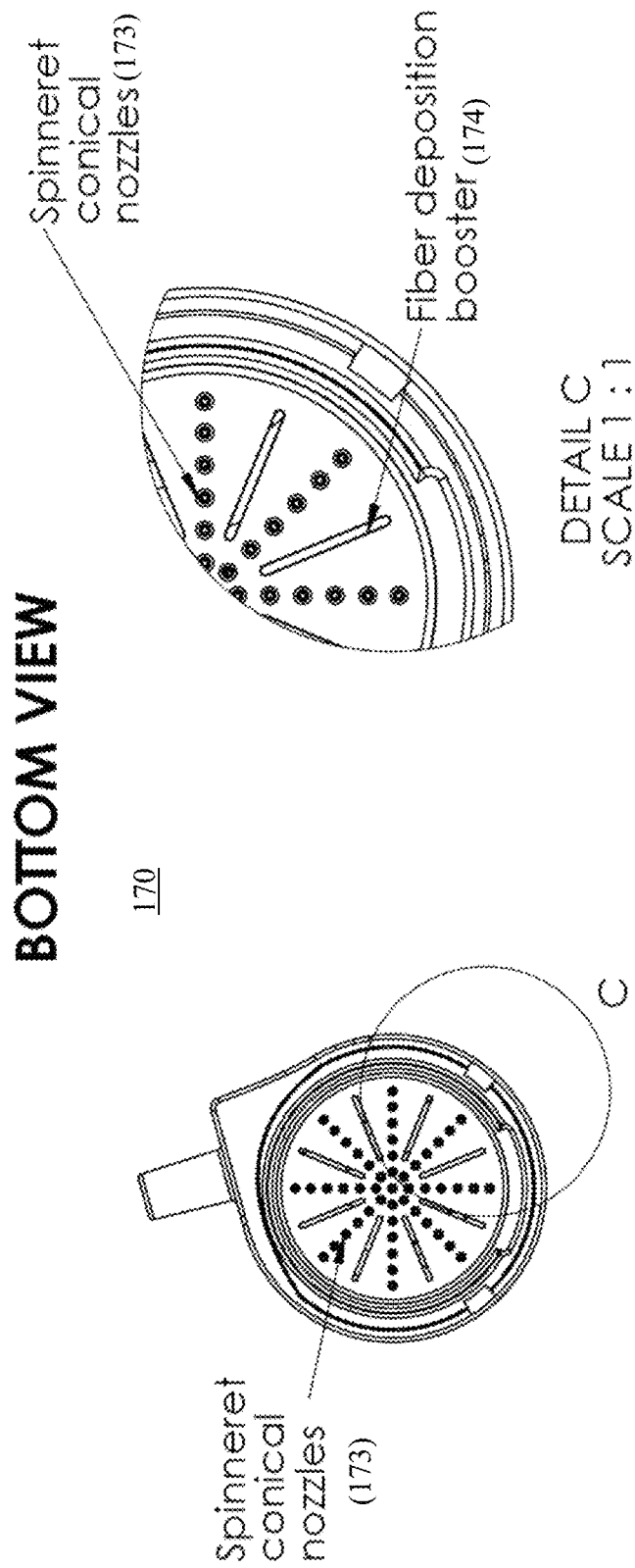
FIG. 8 shows a bottom view (left portion of FIG. 8) and perspective view (of portion C from the left portion of FIG.

FIGS. 7 and 8 show detailed views of the needleless spinneret 170, according to an embodiment of the subject invention. Referring to FIGS. 7 and 8, the needleless spinneret 170 can include a needless spinneret chamber 172, which can contain the solution received from the solution delivery unit 130 (via the solution delivery conduit 160 and/or the spinneret fluid delivery coupler 190). The bottom surface (i.e., the surface that faces away from the glove 110 and towards the target site during use) of the needleless spinneret 170 can include a plurality of spinneret nozzles 173, which may be conical, and one or more fiber deposition boosters 174. The needless spinneret chamber 172 can be disposed over the bottom surface of the needleless spinneret 170, such that the needless spinneret chamber 172 is closer to the glove 110 of the device 100 during use. The nozzles 173 and boosters 174 can be arranged, for example, as shown in FIG. 8, such that lines of nozzles 173 alternate in a circumferential direction around the bottom face of the needleless spinneret 170, and/or the nozzles 173 can include a grouped portion at the center portion of the bottom face of the needleless spinneret 170 (e.g., having a circle of nozzles 173 and a single nozzle 173 in the middle thereof). The bottom face of the needleless spinneret 170 can include, for example, at least five (e.g., eight) boosters 174 and at least five (e.g., eight) lines of nozzles 173. The solution can be forced out of the nozzles 173 and/or the boosters 174 during use, thereby forming a membrane and/or film (from the solution) at the target site during use. The needleless spinneret 170 can further include a solution flow control inlet 171, to which the solution delivery conduit 160 is coupled (e.g., via the spinneret fluid delivery coupler 190; or the spinneret fluid delivery coupler 190 can be omitted and the solution delivery conduit 160 can be coupled directly to the solution flow control inlet 171). The solution flow control inlet 171 can feed directly into the needless spinneret chamber 172. The bottom face (or bottom surface) of the needleless spinneret 170 can be flat (as seen in FIG. 7).

In an embodiment, a method of nanofiber-based membrane (and/or film) fabrication can include providing an electrospinning device 100 having any or all of the features discussed herein. The device 100 can be worn by a user (e.g., on the user's hand) and can be positioned proximate to a target site (e.g., a wound site, a pain site, a site of inflammation, or another site) on a patient (e.g., a mammalian patient, such as a human patient). The patient can be the same as the user (i.e., the user providing a membrane and/or film to himself or herself) or can be different from the user. The device 100 can be positioned such that the needleless spinneret 170 (e.g., the nozzles 173 thereof) face the target site. The device 100 can then be operated to form at least one membrane and/or film on the target site. The membrane (and/or film) can have a thickness in a range of, for example, from 1 nanometer (nm) to 100 micrometers (μm) (or any value or subrange contained therein, such as 1 nm to 10 μm or 1 nm to 5 μm). The membrane (and/or film) can alternatively have a larger thickness (e.g., greater than 100 μm). The user can operate the solution flow control 120, the needleless spinneret 170, and/or the solution delivery unit 130 to have solution provided to the needleless spinneret 170 (via the solution delivery conduit 160, the spinneret fluid delivery coupler 190, and/or the solution flow control inlet 171) and have the needleless spinneret 170 expel the nanofibers and form the membrane (and/or film). The solution can be a drug-loaded (e.g., CBD-loaded) bulk material (e.g., a polymer, such as PVP) solution. The drug(s) and/or bulk material(s) can be dissolved in one or more solvents (e.g., phosphate-buffered saline (PBS) solution). Though CBD, PVP, and PBS solution have been described herein, these are for exemplary purposes only. Any suitable drug, bulk material, or solvent can be used (and more than one of each can be used, or drug(s) can be omitted). The providing of the membrane (and/or film) to the target site can provide wound healing, pain relief, and/or an anti-inflammation effect for the patient. A specific drug can be used in order to provide the desired effect. For example, an anti-inflammatory drug can be used in the solution in order to provide an anti-inflammation effect for the patient.

In order to prepare the electrospinning solution (for the solution delivery unit 130), a uniform mixture solution can be prepared with at least one Food and Drug Administration (FDA)-approved biocompatible and biodegradable bulk material (e.g., polymer) and a drug (e.g., CBD). The ratio of the bulk material to the drug can be in a range of, for example, 1:0.1 to 1:10 (or any value or subrange therein, such as 1:0.3 to 1:1). At least one solvent can be used, and each solvent can have a boiling point of, for example, less than or equal to ≤200° C. The bulk material and any drug present can be dissolved in the at least one solvent to give the electrospinning solution.

The prepared solution can be loaded into the solution delivery unit 130 (e.g., a cartridge), which can be removable and/or disposable. This can be done before or after the user has put on the device. The user can adjust the voltage (e.g., output voltage), pumping rate, and/or pumping time before or during the pumping of the solution. These adjustments can be done, for example, using three adjustable knobs, physical buttons, or smart screen buttons (e.g., on the solution flow control 120, the needleless spinneret 170, and/or the solution delivery unit 130) before or after pressing a start button (or knob). The device can be manually turned off or can be automatically turned off after completing the set time. The user can remove the device and dispose of the solution delivery unit 130 (e.g., the solution delivery unit 130 can be disposable such that someone skilled in the art would understand it is intended for a single-use and is not merely "disposable" only in the sense that anything can theoretically be disposed of).

During use, a battery (e.g., 1 V direct current (DC)) can be applied (e.g., by connecting to the voltage control area 155) can be applied as a fiber generation input power source. The fiber can be deposited at the target site by adjusting the output voltage (e.g., via the solution flow control 120 and/or the needleless spinneret 170) and/or the solution pumping speed (e.g., via the solution flow control 120, the needleless spinneret 170, and/or the solution delivery unit 130).

FIGS. 31 and 32 show views of a wearable, ultralow power, and needleless electrospinning device, according to an embodiment of the subject invention. These figures show the electrospinning process using a 4-nozzle needless spinneret 170 (FIG. 31) and a 6-nozzle needless spinneret 170 (FIG. 32), respectively, for the electrospinning device 100. The smoke-like regions 200 below the nozzles are nanofiber jets and bundles. In the examples shown in FIGS. 31 and 32, the nanofibers are produced using a solution of PVP and CBD (e.g., 0.8:1 ratio of PVP:CBD).

Embodiments of the subject invention can fabricate drug-loaded (e.g., CBD-loaded) fiber-based thin films (e.g., thickness of less than 10 μm). The films can provide pain relief, anti-inflammation, and/or wound healing. Compared to related art electrospinning devices, embodiments of the subject invention can effectively solve the challenges of high applied battery power and imprecision of flow rate control. Embodiments of the subject invention ensure consistent fiber quality with tunable morphologies and a high functional material loading rate, while also allowing the device to be worn directly by the user (e.g., on the hand), thereby reducing direct contact (of the non-glove material) with the skin of the user (compared to handheld or other portable devices).

The devices of embodiments of the subject invention can have low input power (e.g., 1.4 V or less, such as 1 V or less), compared to batteries of 1.5 V-12 V in related art devices. Embodiments of the subject invention can provide precision, such as a flow rate in a range of from 0.07 nanoliters per hour (nl/h) to 0.8 nanoliters per minute (nl/min) (or any value or subrange therein, such as 0.07 nl/h to 0.1 nl/min), compared to 0.831 nl/min to 150.5 milliliters per minute (ml/min) in the related art. The low flow rate allows for excellent precision. Embodiments of the subject invention can provide uniform two-segment diameter distribution with a particle structure (e.g., of the drug(s), such as CBD) having a fiber diameter lower than 2 μm (e.g., lower than 1.1 μm), compared to related art devices that have a fiber diameter of up to 60 μm. Embodiments of the subject invention can provide tunable fiber morphology during the electrospinning process by tuning the output voltages of the bulk material (e.g., polymer) solution parameters. Embodiments of the subject invention can provide and use materials that are biocompatible and biodegradable. The bulk material can include one or more FDA-approved biocompatible and biodegradable polymers with a molecular weight greater than or equal to 5000 grams per mole (g/mol). A single bulk material (e.g., polymer) or multiple bulk materials (e.g., polymers) can be used, depending on the desired application. Embodiments of the subject invention can provide a tunable release profile, with rapid or controlled release based on wound type. The adjustment can be done via the type of bulk material (e.g., the type of polymer) used. Embodiments of the subject invention can provide adaptability, such that a device can be suitable for (and/or configured for) at least one functional matter loading (e.g., CBD). Other nano- or micron-sized small molecular-weight drugs can also be incorporated into the bulk material solution (e.g., polymer solution).

Embodiments of the subject provide electrospinning devices that: are wearable (e.g., hand wearable); have ultralow input power requirement (e.g., 1.4 V or less; can be operated by a single battery for the entire device); and include a novel needleless spinneret. A thin film/layer (e.g., having a length and/or width of at least 3 inches, such as 5 inches) can be generated in 5 minutes or less. The solution can have a high drug loading capability (bulk material to drug ratio of, for example, 1:1, 10-fold high than related art devices). The device is safe due to the insulative glove material, wearable design, and lack of direct contact by any parts other than the insulative glove material during use. The device can have a controllable output voltage range (e.g., in a range of from 5 kilovolts (kV) to 35 kV), ultra-precision solution speed control system (with a flow rate as low as 0.07 nl/h), and uniform two-segment diameter distribution with drug (e.g., CBD) particle structure (fiber diameter lower than 1.1 μm and two-segment diameter distribution) (see also, e.g., FIG. 16).

Embodiments of the subject invention can be used for wound care, such as wound treatment to help the patient recover faster without discomfort and while reducing the risk of infection. Compared to a sterile bandage, ultrasoft, flexible fibers that are adhesive-free can significantly reduce pain caused by abrasion between the wound and the bandage and during bandage removal. Due to ultrahigh surface area, the films formed during use can effectively control bleeding and promote wound healing speed. Due to the low pore size, the films can protect from bacterial or fungi contamination. The used bulk materials (e.g., polymers) can be FDA-approved biocompatible and biodegradable materials. Compared to daily changes of bandages and applied drugs, the formed films can significantly reduce the pain and inconvenience for the patient. Therefore, embodiments of the subject invention could bring wound healing to a new era in which wounds can be directly treated on a hospital bed, on a battlefield, or during a sports game. In addition to CBD, other drugs can be loaded into bulk material fibers. Applications of embodiments of the subject invention include but are not limited to: traumatic wounds caused by accidents or injuries; surgical wounds, especially clean-contaminated wounds, contaminated wounds, and infected wounds; pressure ulcers, especially stages 2-4 with broken open skin; burns, especially second-degree and third-degree burns; diabetic foot ulcers, especially infectious or traumatic ulcers; and disease-triggered ulcers.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

MATERIALS AND METHODS

An electrospinning device as disclosed herein was fabricated, as shown in FIGS. 28-30. A 1 V DC battery was used as a fiber generation input power source. Different types of electrospinning solution were prepared and provided to the device to be electrospun. The fiber was deposited by adjusting the output voltage and/or the solution pumping speed.

Example 1

PVP was dissolved in PBS solution and used as the electrospinning solution. FIGS. 9, 10, and 11 show microscopic images of the resulting PVP fibers. FIG. 15 shows a distribution of the diameter of the PVP fibers; the diameter of the PVP fiber ranged from 0.6 μm to 1.1 μm.

Example 2

The electrospinning solution was prepared by mixing PVP with CBD in a PBS solution. The ratio of PVP to CBD was 1:1. FIGS. 12, 13, and 14 show microscopic images of the resulting PVP/CBD fibers. FIG. 16 shows a distribution of the diameter of the PVP/CBD fibers; the diameter of the PVP/CBD fibers exhibited two-segment distribution, one from 0 μm to 0.4 μm and one from 0.5 μm to 1.1 μm. This two-segment diameter distribution is attributed to the incorporation of CBD drugs. The small drugs were fully dissolved, encapsulated within the fibers or incorporated within the polymer chain structure. The large CBD drugs were particle-shaped (see FIGS. 12-14).

FIGS. 17 and 18 show images of a glove after 1 minute and 5 minutes, respectively, of electrospinning the PVP/CBD fibers.

FIG. 27 shows an image of rapid drug delivery testing on the glove from FIG. 17. The glove from FIG. 17 had the electrospinning done on it with a high flow rate, with the results shown in FIG. 27.

Example 3

The electrospinning solution from Example 2 was repeated but with a gold (Au) coating for the fibers. FIGS. 19 and 21 show microscopic images of the resulting Au-coated PVP/CBD fibers. FIGS. 20 and 22 show energy-dispersive X-ray spectroscopy (EDS) results of the gold (Au)-coated PVP/CBD fibers.

Example 4

The electrospinning solution from Example 2 was repeated but with a ratio of PVP to CBD of 1:0.3. In addition, an electrospinning solution was prepared using only CBD powder. FIGS. 23-25 show Fourier transform infrared spectroscopy (FTIR) results for the PVP/CBD fibers (1:0.3 ratio), CBD powder, the fibers from Example 1, and the fibers from Example 2.

Example 5

The electrospinning solution from Example 2 was repeated, first with 35 milligrams (mg) of PVP/CBD in PBS and then with 80 mg of PVP/CBD in PBS. FIG. 26 shows FTIR results for these.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. An electrospinning device, comprising:
    a glove comprising an electrically insulating material and configured to be worn on a hand of a user;
    a needleless spinneret disposed on a first surface of the glove and configured to produce a nanofiber-based film from a solution by electrospinning;
    a solution delivery unit disposed on the glove and configured to contain the solution;
    a solution delivery conduit connecting the solution delivery unit to the needleless spinneret; and
    a voltage control portion configured to provide power to the electrospinning device.

2. The electrospinning device according to claim 1, further comprising a solution flow control in operable communication with the solution delivery unit and configured to control at least one of a flow rate and a time of solution delivery from the solution delivery unit to the needleless spinneret during use.

3. The electrospinning device according to claim 2, the solution flow control being disposed on a second surface of the glove opposite from the first surface.

4. The electrospinning device according to claim 1, the solution being a polymer solution comprising at least one drug.

5. The electrospinning device according to claim 4, the at least one drug comprising cannabidiol (CBD).

6. The electrospinning device according to claim 1, the voltage control portion comprising exactly one battery configured to provide a voltage of no more than 1.4 Volts (V) to the electrospinning device.

7. The electrospinning device according to claim 1, further comprising a plurality of lights disposed on the first surface of the glove.

8. The electrospinning device according to claim 1, the solution delivery unit being disposable.

9. The electrospinning device according to claim 1, the needleless spinneret comprising:
    a needless spinneret chamber configured to contain the solution;
    a plurality of conical spinneret nozzles on a bottom surface of the needleless spinneret; and
    a plurality of fiber deposition boosters on the bottom surface of the needleless spinneret.

10. The electrospinning device according to claim 9, the plurality of conical spinneret nozzles and the plurality of fiber deposition boosters being disposed such that lines of conical spinneret nozzles alternate with fiber deposition boosters in a circumferential direction around the bottom surface of the needleless spinneret.

11. The electrospinning device according to claim 9, the needleless spinneret further comprising a solution flow control inlet coupled to the solution delivery conduit.

12. The electrospinning device according to claim 1, further comprising a wrist support comprising a rigid material and disposed on at least a second surface of the glove opposite from the first surface.

13. The electrospinning device according to claim 1, the electrospinning device being configured to form a film from the solution at a flow rate in a range of from 0.07 nanoliters per hour (nl/h) to 0.8 nanoliters per minute (nl/min).

14. A method of forming a nanofiber-based film at a target site of a patient, the method comprising:
    providing the electrospinning device according to claim 1;
    providing the solution to the solution delivery unit of the electrospinning device;
    wearing, by the user, the electrospinning device on the hand;
    positioning the electrospinning device proximate to the target site such that a bottom surface of the needleless spinneret faces the target site; and
    operating the electrospinning device such that the needleless spinneret uses the solution and forms the film at the target site.

15. The method according to claim 14, the target site being at least one of a wound site, a pain site, and a site of inflammation, and
    the solution being a polymer solution comprising at least one drug.

16. The method according to claim 15, the at least one drug comprising cannabidiol (CBD).

17. The method according to claim 14, the electrospinning device operating using a total voltage of no more than 1.4 Volts (V),
    the needleless spinneret forming the film at the target site at a flow rate in a range of from 0.07 nanoliters per hour (nl/h) to 0.8 nanoliters per minute (nl/min), and
    the film having a thickness in a range of from 1 nanometer (nm) to 10 micrometers (μm).

18. An electrospinning device, comprising:
    a glove comprising an electrically insulating material and configured to be worn on a hand of a user;
    a needleless spinneret disposed on a first surface of the glove and configured to produce a nanofiber-based film from a solution by electrospinning;
    a solution delivery unit disposed on the glove and configured to contain the solution;

a solution delivery conduit connecting the solution delivery unit to the needleless spinneret;
a solution flow control in operable communication with the solution delivery unit and configured to control at least one of a flow rate and a time of solution delivery from the solution delivery unit to the needleless spinneret during use;
a voltage control portion configured to provide power to the electrospinning device;
a plurality of lights disposed on the first surface of the glove; and
a wrist support comprising a rigid material and disposed on at least the second surface of the glove,
the solution flow control being disposed on a second surface of the glove opposite from the first surface,
the solution being a polymer solution comprising at least one drug,
the voltage control portion comprising exactly one battery configured to provide a voltage of no more than 1.4 Volts (V) to the electrospinning device,
the solution delivery unit being disposable,
the needleless spinneret comprising:
  a needless spinneret chamber configured to contain the solution;
  a plurality of conical spinneret nozzles on a bottom surface of the needleless spinneret;
  a plurality of fiber deposition boosters on the bottom surface of the needleless spinneret; and
  a solution flow control inlet coupled to the solution delivery conduit,
the plurality of conical spinneret nozzles and the plurality of fiber deposition boosters being disposed such that lines of conical spinneret nozzles alternate with fiber deposition boosters in a circumferential direction around the bottom surface of the needleless spinneret, and
the electrospinning device being configured to form a film from the solution at a flow rate in a range of from 0.07 nanoliters per hour (nl/h) to 0.8 nanoliters per minute (nl/min).

19. The electrospinning device according to claim 18, the at least one drug comprising cannabidiol (CBD).

20. A method of forming a nanofiber-based film at a target site of a patient, the method comprising:
providing the electrospinning device according to claim 19;
providing the solution to the solution delivery unit of the electrospinning device;
wearing, by the user, the electrospinning device on the hand;
positioning the electrospinning device proximate to the target site such that a bottom surface of the needleless spinneret faces the target site;
operating the electrospinning device such that the needleless spinneret uses the solution and forms the film at the target site,
the target site being at least one of a wound site, a pain site, and a site of inflammation,
the electrospinning device operating using a total voltage of no more than 1.4 V, the needleless spinneret forming the film at the target site at a flow rate in a range of from 0.07 nl/h to 0.8 nl/min, and
the film having a thickness in a range of from 1 nanometer (nm) to 10 micrometers (μm).

* * * * *